United States Patent
Anderson et al.

(10) Patent No.: US 11,890,018 B2
(45) Date of Patent: *Feb. 6, 2024

(54) OCCLUSIVE DEVICE WITH ACTUATABLE FIXATION MEMBERS

(71) Applicant: BOSTON SCIENTIFIC SCIMED, INC., Maple Grove, MN (US)

(72) Inventors: James M. Anderson, Corcoran, MN (US); Uchenna Junior Agu, Baton Rouge, LA (US); David John Onushko, Maple Grove, MN (US); Lloyd Radman, Blaine, MN (US); Jose A. Meregotte, Vadnais Heights, MN (US); John M. Edgell, Plymouth, MN (US); David Raab, Roseville, MN (US); Joshua Mark Inouye, Maple Grove, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 121 days.

This patent is subject to a terminal disclaimer.

(21) Appl. No.: 17/475,762

(22) Filed: Sep. 15, 2021

(65) Prior Publication Data

US 2022/0000488 A1 Jan. 6, 2022

Related U.S. Application Data

(63) Continuation of application No. 16/434,683, filed on Jun. 7, 2019, now Pat. No. 11,123,079.

(Continued)

(51) Int. Cl.
*A61B 17/12* (2006.01)
*A61B 17/00* (2006.01)

(52) U.S. Cl.
CPC ............... *A61B 17/12122* (2013.01); *A61B 17/12136* (2013.01); *A61B 2017/00557* (2013.01);

(Continued)

(58) Field of Classification Search
CPC ........ A61B 17/12031; A61B 17/12122; A61B 17/12136; A61B 2017/00557;

(Continued)

(56) References Cited

U.S. PATENT DOCUMENTS

| 1,782,830 A | 6/1876 | French |
| 1,967,318 A | 10/1931 | Monahan |

(Continued)

FOREIGN PATENT DOCUMENTS

| CN | 106859722 A | 6/2017 |
| WO | 9313712 A1 | 7/1993 |

(Continued)

OTHER PUBLICATIONS

International Search Report and Written Opinion dated Sep. 26, 2019 for International Application PCT/US2019/036085.

(Continued)

*Primary Examiner* — Jocelin C Tanner
(74) *Attorney, Agent, or Firm* — Seager, Tufte & Wickhem LLP

(57) ABSTRACT

An example medical device for occluding the left atrial appendage is disclosed. The example medical device for occluding the left atrial appendage includes an expandable member having a first end region, a second end region and an inflation cavity. The example medical device includes at least one fixation member having a first end and a second end coupled to the expandable member. The at least one fixation member is configured to move from a delivery configuration to a deployed configuration in response to an expansion of the expandable member. Additionally, the (Continued)

example medical device includes a valve member extending at least partially into the inflation cavity and the expandable member is configured to expand and seal the opening of the left atrial appendage.

13 Claims, 26 Drawing Sheets

Related U.S. Application Data

(60) Provisional application No. 62/682,206, filed on Jun. 8, 2018.

(52) U.S. Cl.
CPC .............. *A61B 2017/00632* (2013.01); *A61B 2017/12054* (2013.01)

(58) Field of Classification Search
CPC ........... A61B 2017/00632; A61B 2017/12054; A61B 2017/12095
See application file for complete search history.

(56) References Cited

U.S. PATENT DOCUMENTS

| | | |
|---|---|---|
| 3,402,710 A | 9/1968 | Paleshuck |
| 3,540,431 A | 11/1970 | Mobin-Uddin |
| 3,638,652 A | 2/1972 | Kelley |
| 3,844,302 A | 10/1974 | Klein |
| 3,874,388 A | 4/1975 | King |
| 4,007,743 A | 2/1977 | Blake |
| 4,309,776 A | 1/1982 | Berguer |
| 4,341,218 A | 7/1982 | U |
| 4,364,392 A | 12/1982 | Strother et al. |
| 4,545,367 A | 10/1985 | Tucci |
| 4,585,000 A | 4/1986 | Hershenson |
| 4,603,693 A | 8/1986 | Conta et al. |
| 4,611,594 A | 9/1986 | Grayhack et al. |
| 4,619,246 A | 10/1986 | Molgaard-Nielsen et al. |
| 4,638,803 A | 1/1987 | Rand |
| 4,665,906 A | 5/1987 | Jervis |
| 4,681,588 A | 7/1987 | Ketharanathan |
| 4,710,192 A | 12/1987 | Liotta et al. |
| 4,793,348 A | 12/1988 | Palmaz |
| 4,832,055 A | 5/1989 | Palestrant |
| 4,917,089 A | 4/1990 | Sideris |
| 4,921,484 A | 5/1990 | Hillstead |
| 5,037,810 A | 8/1991 | Saliba, Jr. |
| 5,041,090 A | 8/1991 | Scheglov et al. |
| 5,041,093 A | 8/1991 | Chu |
| 5,042,707 A | 8/1991 | Taheri |
| 5,053,009 A | 10/1991 | Herzberg |
| 5,064,435 A | 11/1991 | Porter |
| 5,071,407 A | 12/1991 | Termin et al. |
| 5,078,736 A | 1/1992 | Behl |
| 5,098,440 A | 3/1992 | Hillstead |
| 5,108,420 A | 4/1992 | Marks |
| 5,116,360 A | 5/1992 | Pinchuk et al. |
| 5,122,136 A | 6/1992 | Guglielmi et al. |
| 5,171,259 A | 12/1992 | Inoue |
| 5,176,692 A | 1/1993 | Wilk et al. |
| 5,192,301 A | 3/1993 | Kamiya et al. |
| 5,234,458 A | 8/1993 | Metais |
| 5,256,146 A | 10/1993 | Ensminger et al. |
| 5,258,000 A | 11/1993 | Gianturco |
| 5,258,042 A | 11/1993 | Mehta |
| 5,284,488 A | 2/1994 | Sideris |
| 5,304,184 A | 4/1994 | Hathaway et al. |
| 5,306,234 A | 4/1994 | Johnson |
| 5,334,217 A | 8/1994 | Das |
| 5,350,398 A | 9/1994 | Pavcnik et al. |
| 5,350,399 A | 9/1994 | Erlebacher et al. |
| 5,353,784 A | 10/1994 | Nady-Mohamed |
| 5,366,460 A | 11/1994 | Eberbach |
| 5,366,504 A | 11/1994 | Andersen et al. |
| 5,370,657 A | 12/1994 | Irie |
| 5,375,612 A | 12/1994 | Cottenceau et al. |
| 5,397,355 A | 3/1995 | Marin et al. |
| 5,409,444 A | 4/1995 | Kensey et al. |
| 5,417,699 A | 5/1995 | Klein et al. |
| 5,421,832 A | 6/1995 | Lefebvre |
| 5,425,744 A | 6/1995 | Fagan et al. |
| 5,433,727 A | 7/1995 | Sideris |
| 5,443,454 A | 8/1995 | Tanabe et al. |
| 5,443,478 A | 8/1995 | Purdy |
| 5,451,235 A | 9/1995 | Lock et al. |
| 5,464,408 A | 11/1995 | Duc |
| 5,469,867 A | 11/1995 | Schmitt |
| 5,490,856 A | 2/1996 | Person et al. |
| 5,522,790 A | 6/1996 | Moll et al. |
| 5,522,822 A | 6/1996 | Phelps et al. |
| 5,522,836 A | 6/1996 | Palermo |
| 5,527,322 A | 6/1996 | Klein et al. |
| 5,527,338 A | 6/1996 | Purdy |
| 5,569,204 A | 10/1996 | Cramer |
| 5,591,196 A | 1/1997 | Marin et al. |
| 5,614,204 A | 3/1997 | Cochrum |
| 5,634,936 A | 6/1997 | Linden et al. |
| 5,634,942 A | 6/1997 | Chevillon et al. |
| 5,637,097 A | 6/1997 | Yoon |
| 5,643,282 A | 7/1997 | Kieturakis |
| 5,643,292 A | 7/1997 | Hart |
| 5,649,953 A | 7/1997 | Lefebvre |
| 5,653,690 A | 8/1997 | Booth et al. |
| 5,662,671 A | 9/1997 | Barbut et al. |
| 5,669,933 A | 9/1997 | Simon et al. |
| 5,681,347 A | 10/1997 | Cathcart et al. |
| 5,690,671 A | 11/1997 | McGurk et al. |
| 5,693,067 A | 12/1997 | Purdy |
| 5,695,525 A | 12/1997 | Mulhauser et al. |
| 5,700,285 A | 12/1997 | Myers et al. |
| 5,702,421 A | 12/1997 | Schneidt |
| 5,709,224 A | 1/1998 | Behl et al. |
| 5,709,704 A | 1/1998 | Nott et al. |
| 5,709,707 A | 1/1998 | Lock et al. |
| 5,725,552 A | 3/1998 | Kotula et al. |
| 5,725,568 A | 3/1998 | Hastings |
| 5,733,294 A | 3/1998 | Forber et al. |
| 5,733,302 A | 3/1998 | Myler et al. |
| 5,735,290 A | 4/1998 | Sterman et al. |
| 5,749,883 A | 5/1998 | Halpern |
| 5,749,894 A | 5/1998 | Engelson |
| 5,766,219 A | 6/1998 | Horton |
| 5,769,816 A | 6/1998 | Barbut et al. |
| 5,776,097 A | 7/1998 | Massoud |
| 5,782,860 A | 7/1998 | Epstein et al. |
| 5,785,679 A | 7/1998 | Abolfathi et al. |
| 5,800,457 A | 9/1998 | Gelbfish |
| 5,800,512 A | 9/1998 | Lentz et al. |
| 5,810,874 A | 9/1998 | Lefebvre |
| 5,823,198 A | 10/1998 | Jones et al. |
| 5,830,228 A | 11/1998 | Knapp et al. |
| 5,836,913 A | 11/1998 | Orth et al. |
| 5,836,968 A | 11/1998 | Simon et al. |
| 5,843,118 A | 12/1998 | Sepetka et al. |
| 5,846,260 A | 12/1998 | Maahs |
| 5,846,261 A | 12/1998 | Kotula et al. |
| 5,849,005 A | 12/1998 | Garrison |
| 5,851,232 A | 12/1998 | Lois |
| 5,853,422 A | 12/1998 | Huebsch et al. |
| 5,855,597 A | 1/1999 | Jayaraman |
| 5,865,791 A | 2/1999 | Whayne et al. |
| 5,865,802 A | 2/1999 | Yoon et al. |
| 5,868,708 A | 2/1999 | Hart et al. |
| 5,876,367 A | 3/1999 | Kaganov et al. |
| 5,879,366 A | 3/1999 | Shaw et al. |
| 5,882,340 A | 3/1999 | Yoon |
| 5,885,258 A | 3/1999 | Sachdeva et al. |
| 5,891,558 A | 4/1999 | Bell et al. |
| 5,895,399 A | 4/1999 | Barbut et al. |
| 5,904,680 A | 5/1999 | Kordis et al. |
| 5,904,703 A | 5/1999 | Gilson |
| 5,906,207 A | 5/1999 | Shen |

(56) References Cited

U.S. PATENT DOCUMENTS

| | | | |
|---|---|---|---|
| 5,910,154 A | 6/1999 | Tsugita et al. |
| 5,911,734 A | 6/1999 | Tsugita et al. |
| 5,916,236 A | 6/1999 | Muijs Van De Moer et al. |
| 5,928,192 A | 7/1999 | Maahs |
| 5,928,260 A | 7/1999 | Chin et al. |
| 5,935,145 A | 8/1999 | Villar et al. |
| 5,935,147 A | 8/1999 | Kensey et al. |
| 5,935,148 A | 8/1999 | Villar et al. |
| 5,941,249 A | 8/1999 | Maynard |
| 5,944,738 A | 8/1999 | Amplatz et al. |
| 5,947,997 A | 9/1999 | Pavcnik et al. |
| 5,951,589 A | 9/1999 | Epstein et al. |
| 5,951,599 A | 9/1999 | McCrory |
| 5,954,694 A | 9/1999 | Sunseri |
| 5,957,940 A | 9/1999 | Tanner et al. |
| 5,961,545 A | 10/1999 | Lentz et al. |
| 5,976,174 A | 11/1999 | Ruiz |
| 5,980,514 A | 11/1999 | Kupiecki et al. |
| 5,980,555 A | 11/1999 | Barbut et al. |
| 5,989,281 A | 11/1999 | Barbut et al. |
| 5,993,469 A | 11/1999 | McKenzie et al. |
| 5,993,483 A | 11/1999 | Gianotti |
| 5,997,557 A | 12/1999 | Barbut et al. |
| 6,004,348 A | 12/1999 | Banas et al. |
| 6,007,523 A | 12/1999 | Mangosong |
| 6,007,557 A | 12/1999 | Ambrisco et al. |
| 6,010,517 A | 1/2000 | Baccaro |
| 6,010,522 A | 1/2000 | Barbut et al. |
| 6,013,093 A | 1/2000 | Nott et al. |
| 6,024,754 A | 2/2000 | Engelson |
| 6,024,755 A | 2/2000 | Addis |
| 6,024,756 A | 2/2000 | Huebsch et al. |
| 6,027,520 A | 2/2000 | Tsugita et al. |
| 6,033,420 A | 3/2000 | Hahnen |
| 6,042,598 A | 3/2000 | Tsugita et al. |
| 6,048,331 A | 4/2000 | Tsugita et al. |
| 6,051,014 A | 4/2000 | Jang |
| 6,051,015 A | 4/2000 | Maahs |
| 6,056,720 A | 5/2000 | Morse |
| 6,063,070 A | 5/2000 | Eder |
| 6,068,621 A | 5/2000 | Balceta et al. |
| 6,074,357 A | 6/2000 | Kaganov et al. |
| 6,076,012 A | 6/2000 | Swanson et al. |
| 6,079,414 A | 6/2000 | Roth |
| 6,080,182 A | 6/2000 | Shaw et al. |
| 6,080,183 A | 6/2000 | Tsugita et al. |
| 6,083,239 A | 7/2000 | Addis |
| 6,096,053 A | 8/2000 | Bates |
| 6,110,243 A | 8/2000 | Wnenchak et al. |
| 6,124,523 A | 9/2000 | Banas et al. |
| 6,132,438 A | 10/2000 | Fleischman et al. |
| 6,135,991 A | 10/2000 | Muni et al. |
| 6,136,016 A | 10/2000 | Barbut et al. |
| 6,139,527 A | 10/2000 | Laufer et al. |
| 6,139,573 A | 10/2000 | Sogard et al. |
| 6,152,144 A | 11/2000 | Lesh et al. |
| 6,156,055 A | 12/2000 | Ravenscroft |
| 6,161,543 A | 12/2000 | Cox et al. |
| 6,171,329 B1 | 1/2001 | Shaw et al. |
| 6,179,859 B1 | 1/2001 | Bates et al. |
| 6,214,029 B1 | 4/2001 | Thill et al. |
| 6,231,561 B1 | 5/2001 | Frazier et al. |
| 6,231,589 B1 | 5/2001 | Wessman et al. |
| 6,251,122 B1 | 6/2001 | Tsukernik |
| 6,258,115 B1 | 7/2001 | Dubrul |
| 6,270,490 B1 | 8/2001 | Hahnen |
| 6,277,138 B1 | 8/2001 | Levinson et al. |
| 6,290,674 B1 | 9/2001 | Roue et al. |
| 6,319,251 B1 | 11/2001 | Tu et al. |
| 6,328,727 B1 | 12/2001 | Frazier et al. |
| 6,342,062 B1 | 1/2002 | Suon et al. |
| 6,346,116 B1 | 2/2002 | Brooks et al. |
| 6,364,895 B1 | 4/2002 | Greenhalgh |
| 6,368,338 B1 | 4/2002 | Knya et al. |
| 6,371,971 B1 | 4/2002 | Tsugita et al. |
| 6,375,670 B1 | 4/2002 | Greenhalgh |
| 6,391,044 B1 | 5/2002 | Yadav et al. |
| 6,402,746 B1 | 6/2002 | Whayne et al. |
| 6,419,669 B1 | 7/2002 | Frazier et al. |
| 6,440,152 B1 | 8/2002 | Gainor et al. |
| 6,443,972 B1 | 9/2002 | Bosma et al. |
| 6,447,530 B1 | 9/2002 | Ostrovsky et al. |
| 6,468,291 B2 | 10/2002 | Bates et al. |
| 6,511,496 B1 | 1/2003 | Huter et al. |
| 6,517,573 B1 | 2/2003 | Pollock et al. |
| 6,547,760 B1 | 4/2003 | Samson et al. |
| 6,551,303 B1 | 4/2003 | Van Tassel et al. |
| 6,551,344 B2 | 4/2003 | Thill |
| 6,558,405 B1 | 5/2003 | McInnes |
| 6,562,058 B2 | 5/2003 | Seguin et al. |
| 6,599,308 B2 | 7/2003 | Amplatz |
| 6,652,555 B1 | 11/2003 | VanTassel et al. |
| 6,652,556 B1 | 11/2003 | VanTassel et al. |
| 6,689,150 B1 | 2/2004 | VanTassel et al. |
| 6,730,108 B2 | 5/2004 | Van Tassel et al. |
| 6,837,901 B2 * | 1/2005 | Rabkin ............... A61B 17/221 623/1.11 |
| 6,855,153 B2 | 2/2005 | Saadat |
| 6,949,113 B2 | 9/2005 | Van Tassel et al. |
| 6,994,092 B2 | 2/2006 | van der Burg et al. |
| 7,011,671 B2 | 3/2006 | Welch |
| 7,044,134 B2 | 5/2006 | Khairkhahan et al. |
| 7,128,073 B1 | 10/2006 | van der Burg et al. |
| 8,062,282 B2 | 11/2011 | Kolb |
| 8,491,623 B2 | 7/2013 | Vogel et al. |
| 11,123,079 B2 * | 9/2021 | Anderson ......... A61B 17/12122 |
| 2001/0034537 A1 | 10/2001 | Shaw et al. |
| 2002/0022860 A1 | 2/2002 | Borillo et al. |
| 2002/0035374 A1 | 3/2002 | Borillo et al. |
| 2002/0062133 A1 | 5/2002 | Gilson et al. |
| 2002/0082638 A1 | 6/2002 | Porter et al. |
| 2002/0138094 A1 | 9/2002 | Borillo et al. |
| 2002/0138097 A1 | 9/2002 | Ostrovsky et al. |
| 2003/0023266 A1 | 1/2003 | Borillo et al. |
| 2003/0057156 A1 | 3/2003 | Peterson et al. |
| 2003/0181942 A1 | 9/2003 | Sutton et al. |
| 2003/0220666 A1 | 11/2003 | Mirigian et al. |
| 2003/0220667 A1 | 11/2003 | van der Burg et al. |
| 2004/0098031 A1 | 5/2004 | van der Burg et al. |
| 2004/0215230 A1 | 10/2004 | Frazier et al. |
| 2005/0004652 A1 | 1/2005 | van der Burg et al. |
| 2005/0113861 A1 | 5/2005 | Corcoran et al. |
| 2005/0203568 A1 | 9/2005 | Burg et al. |
| 2010/0324588 A1 * | 12/2010 | Miles ............... A61B 17/12122 606/198 |
| 2013/0073029 A1 * | 3/2013 | Shaw ............... A61B 17/12122 623/1.36 |
| 2014/0039536 A1 | 2/2014 | Cully et al. |
| 2014/0100596 A1 | 4/2014 | Rudman et al. |
| 2014/0336612 A1 | 11/2014 | Frydlewski et al. |
| 2016/0106437 A1 | 4/2016 | Van Der Burg et al. |
| 2016/0287259 A1 | 10/2016 | Hanson et al. |
| 2017/0042549 A1 * | 2/2017 | Kaplan ............ A61B 17/12145 |
| 2017/0042550 A1 | 2/2017 | Chakraborty et al. |
| 2018/0116678 A1 * | 5/2018 | Melanson ......... A61B 17/12122 |
| 2019/0183509 A1 | 6/2019 | Anderson et al. |
| 2019/0223883 A1 | 7/2019 | Anderson et al. |

FOREIGN PATENT DOCUMENTS

| | | | |
|---|---|---|---|
| WO | 9640356 A1 | 12/1996 |
| WO | 9721402 A1 | 6/1997 |
| WO | 9728749 A1 | 8/1997 |
| WO | 9802100 A1 | 1/1998 |
| WO | 9817187 A1 | 4/1998 |
| WO | 9823322 A1 | 6/1998 |
| WO | 9827868 A1 | 7/1998 |
| WO | 9907289 A1 | 2/1999 |
| WO | 9908607 A1 | 2/1999 |
| WO | 9930640 A1 | 6/1999 |
| WO | 9944510 A1 | 9/1999 |
| WO | 0016705 A1 | 3/2000 |
| WO | 0027292 A1 | 5/2000 |
| WO | 0067669 A1 | 11/2000 |

(56) References Cited

FOREIGN PATENT DOCUMENTS

| WO | 0115629 A1 | 3/2001 |
|----|------------|--------|
| WO | 0121247 A1 | 3/2001 |
| WO | 0130266 A1 | 5/2001 |
| WO | 0130267 A1 | 5/2001 |
| WO | 0130268 A1 | 5/2001 |
| WO | 0215793 A1 | 2/2002 |
| WO | 0224106 A2 | 3/2002 |
| WO | 03032818 A2 | 4/2003 |
| WO | 2015164836 A1 | 10/2015 |
| WO | 2018017935 A1 | 1/2018 |
| WO | 2018187732 A1 | 10/2018 |

OTHER PUBLICATIONS

PCT Search Report from co-pending Application PCT/US02/33808 dated May 20, 2003.
PCT Search Report from PCT/US99/26325 dated Feb. 15, 2000.
Cragg et al; "Nonsurgical Placement of Arterial Endoprosthesis: A New Technique Using Nitinol Wire," Radiology vol. 147, No. 1 pp. 261-263, Apr. 1983.
Cragg et al; "A New Percutaneous Vena Cava Filter", ALJ, 141: 601-604, Sep. 1983.
Sugita et al; "Nonsurgical Implantation of a Vascular Ring Prosthesis Using Thermal Shape Memory Ti/Ni Alloy (Nitinol Wire)," Trans. Am. Soc. Artif. Intern. Organs, vol. XXXII, 30-34, 1986.
Ruttenberg, Nonsurgical Therapy of Cardiac Disorders, Pediatric Consult, vol. 5, No. 2, pages not numbered, 1986.
Rashkind et al; Nonsurgical Closure of Patent Ductus Arteriosus: Clinical Application of the Rashkind PDA Occluder System, Circulation 75, No. 3, 583-592-1987.
Lock et al; "Transcatheter Umbrella Closure of Congenital Heart Defects," Circulation, vol. 75, No. 3, 593-599, 1987.
Lock et al; "Transcatheter Closure of Artrial Septal Defects," Circulation, vol. 79, No. 5 1091-1099, May 1989.
Wessel et al; "Outpatient Closure of the Patent Ductus Arteriosus," Circulation, vol. 77, No. 5 1068-1071, 1988.
Invite to Pay Additional Fees dated Feb. 22, 2019 for International Application No. PCT/US2018/066163.
International Search Report and Written Opinion dated Sep. 9, 2019 for International Application No. PCT/US2019/033698.

* cited by examiner

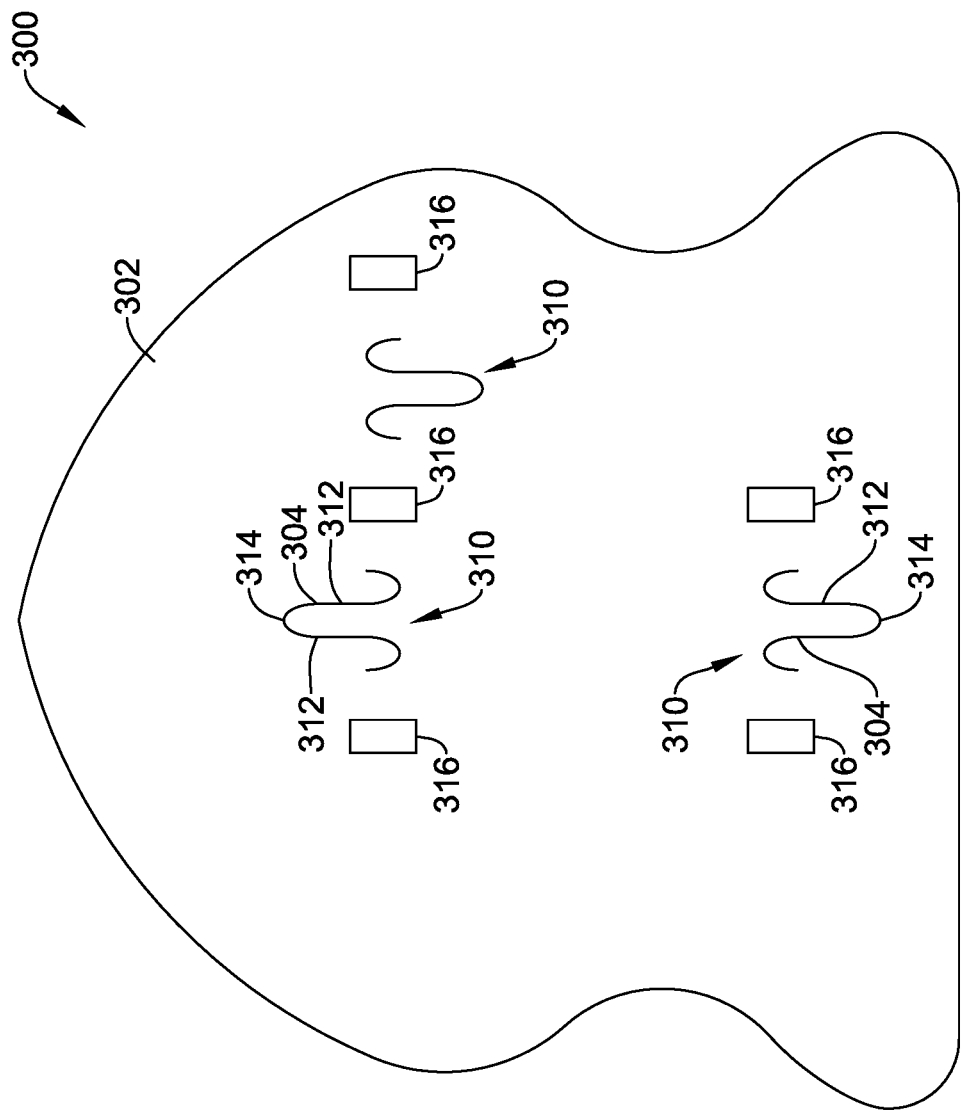

OCCLUSIVE DEVICE WITH ACTUATABLE FIXATION MEMBERS

CROSS-REFERENCE TO RELATED APPLICATIONS

This application claims the benefit of U.S. application Ser. No. 16/434,683, filed Jun. 7, 2019, which claims benefit of priority under 35 U.S.C. § 119 to U.S. Provisional Application Ser. No. 62/682,206, filed Jun. 8, 2018, the entirety of which is incorporated herein by reference.

BACKGROUND

The left atrial appendage (LAA) is a small organ attached to the left atrium of the heart as a pouch-like extension. In patients suffering from atrial fibrillation, the left atrial appendage may not properly contract with the left atrium, causing stagnant blood to pool within its interior, which can lead to the undesirable formation of thrombi within the left atrial appendage. Thrombi forming in the left atrial appendage may break loose from this area and enter the blood stream. Thrombi that migrate through the blood vessels may eventually plug a smaller vessel downstream and thereby contribute to stroke or heart attack. Clinical studies have shown that the majority of blood clots in patients with atrial fibrillation are found in the left atrial appendage. As a treatment, medical devices have been developed which are positioned in the left atrial appendage and deployed to close off the ostium of the left atrial appendage. Over time, the exposed surface(s) spanning the ostium of the left atrial appendage becomes covered with tissue (a process called endothelization), effectively removing the left atrial appendage from the circulatory system and reducing or eliminating the number of thrombi which may enter the blood stream from the left atrial appendage. A continuing need exists for improved medical devices and methods to control thrombus formation within the left atrial appendage of patients suffering from atrial fibrillation.

SUMMARY

This disclosure provides design, material, manufacturing method, and use alternatives for medical devices. An example medical device for occluding the left atrial appendage may comprise an expandable member having a first end region, a second end region and an inflation cavity, at least one fixation member having a first end and a second end coupled to the expandable member, the at least one fixation member configured to move from a delivery configuration to a deployed configuration in response to an expansion of the expandable member, and a valve member extending at least partially into the inflation cavity. The expandable member may be configured to expand and seal the opening of the left atrial appendage.

Alternatively or additionally to any of the examples above, in another example, the first end of the at least one fixation member may be configured to engage a tissue when the at least one fixation member is in the deployed configuration.

Alternatively or additionally to any of the examples above, in another example, when the at least one fixation member is in the delivery configuration the first end of the at least one fixation member may extend approximately parallel to a longitudinal axis of the expandable member and when the at least one fixation member is in the deployed configuration the first end of the at least one fixation member may extend at a non-parallel angle to the longitudinal axis and radially away from an outer surface of the expandable member.

Alternatively or additionally to any of the examples above, in another example, the first end of the at least one fixation member may be pre-formed to extend radially away from the outer surface of the expandable member.

Alternatively or additionally to any of the examples above, in another example, the medical device may further comprise a first retention sheath coupled to an outer surface of the expandable member.

Alternatively or additionally to any of the examples above, in another example, the first retention sheath may include a cavity.

Alternatively or additionally to any of the examples above, in another example, when the at least one fixation member is in the delivery configuration the first end of the at least one fixation member may be disposed within the cavity of the first retention sheath and biased into the delivery configuration.

Alternatively or additionally to any of the examples above, in another example, the medical device may further comprise a first retention sheath defining a lumen and coupled to an outer surface of the expandable member and a second retention sheath defining a lumen and coupled to the outer surface of the expandable member, the first and second retention sheath longitudinally aligned.

Alternatively or additionally to any of the examples above, in another example, the at least one fixation member may comprise a first fixation member and a second fixation member.

Alternatively or additionally to any of the examples above, in another example, when the first and second fixation members are in the delivery configuration a first end of the first fixation member may be disposed within the lumen of the second retention sheath, an intermediate portion of the first fixation member may be disposed within the lumen of the first retention sheath, a first end of the second fixation member may be disposed within the lumen of the first retention sheath, and an intermediate portion of the second fixation member may be disposed within the lumen of the second retention sheath.

Alternatively or additionally to any of the examples above, in another example, the at least one fixation member may have a generally "U"-shaped configuration having a pair of legs and a curved connection region, an end of each leg of the pair of legs defining the first end and the curved connection region defining the second end.

Alternatively or additionally to any of the examples above, in another example, the second end may be embedded in a securement rib, the securement rib extending circumferentially about the expandable member and in the delivery configuration the first end may be disposed within a cavity in a sheathing rib extending circumferentially about the expandable member and longitudinally spaced from the securement rib.

Alternatively or additionally to any of the examples above, in another example, the second end may be coupled to an outer surface of the expandable member and in the delivery configuration the end of a first leg of the pair of legs may be disposed within a cavity of a first securement member and the end of a second leg of the pair of legs may be disposed within a cavity of a second securement member, the second securement member circumferentially spaced from the first securement member.

Alternatively or additionally to any of the examples above, in another example, the expandable member may include at least an inner layer and an outer layer.

Alternatively or additionally to any of the examples above, in another example, the at least one fixation member may be coupled to the inner layer and may be configured to extend through an aperture in the outer layer when the at least one fixation member is in the deployed configuration.

In another example, a medical device for occluding the left atrial appendage may comprise an expandable member having a first end region, a second end region and an inflation cavity, at least one fixation member having a first end and a second end coupled to the expandable member, the at least one fixation member configured to move from a delivery configuration to a deployed configuration in response to an expansion of the expandable member, and a valve member extending at least partially into the inflation cavity. The expandable member may be configured to expand and seal the opening of the left atrial appendage.

Alternatively or additionally to any of the examples above, in another example, the first end of the at least one fixation member may be configured to engage a tissue when the at least one fixation member is in the deployed configuration.

Alternatively or additionally to any of the examples above, in another example, when the at least one fixation member is in the delivery configuration the first end of the at least one fixation member may extend approximately parallel to a longitudinal axis of the expandable member and when the at least one fixation member is in the deployed configuration the first end of the at least one fixation member may extend at a non-parallel angle to the longitudinal axis and radially away from an outer surface of the expandable member.

Alternatively or additionally to any of the examples above, in another example, the first end of the at least one fixation member may be pre-formed to extend radially away from the outer surface of the expandable member.

Alternatively or additionally to any of the examples above, in another example, the medical device may further comprise a first retention sheath coupled to an outer surface of the expandable member.

Alternatively or additionally to any of the examples above, in another example, the first retention sheath may include a cavity.

Alternatively or additionally to any of the examples above, in another example, when the at least one fixation member is in the delivery configuration the first end of the at least one fixation member may be disposed within the cavity of the first retention sheath and biased into the delivery configuration.

Alternatively or additionally to any of the examples above, in another example, the medical device may further comprise a first retention sheath defining a lumen and coupled to an outer surface of the expandable member and a second retention sheath defining a lumen and coupled to the outer surface of the expandable member, the first and second retention sheath longitudinally aligned.

Alternatively or additionally to any of the examples above, in another example, the at least one fixation member may comprise a first fixation member and a second fixation member.

Alternatively or additionally to any of the examples above, in another example, when the first and second fixation members are in the delivery configuration a first end of the first fixation member may be disposed within the lumen of the second retention sheath, an intermediate portion of the first fixation member may be disposed within the lumen of the first retention sheath, a first end of the second fixation member may be disposed within the lumen of the first retention sheath, and an intermediate portion of the second fixation member may be disposed within the lumen of the second retention sheath.

In another example, a medical device for occluding the left atrial appendage may comprise an expandable member having a first end region, a second end region and an inflation cavity, at least one fixation member having a first leg, a second leg, and a curved connection region connecting a second end of the first leg and a second end of the second leg, the at least one fixation member configured to move from a delivery configuration to a deployed configuration in response to an expansion of the expandable member, and a valve member extending at least partially into the inflation cavity. The expandable member may be configured to expand and seal the opening of the left atrial appendage.

Alternatively or additionally to any of the examples above, in another example, a first end of the first leg and a first end of the second leg may each be pre-formed to extend radially away from an outer surface of the expandable member.

Alternatively or additionally to any of the examples above, in another example, the curved connection region may be embedded in a securement rib, the securement rib extending circumferentially about the expandable member.

Alternatively or additionally to any of the examples above, in another example, when in the delivery configuration the first ends of the first and second legs may be disposed within a cavity in a sheathing rib extending circumferentially about the expandable member and longitudinally spaced from the securement rib.

Alternatively or additionally to any of the examples above, in another example, the curved connection region may be coupled to the outer surface of the expandable member.

Alternatively or additionally to any of the examples above, in another example, when in the delivery configuration the first ends of the first and second legs may be disposed within a cavity in a first securement member and a cavity in a second securement member, respectively, the second securement member circumferentially spaced from the first securement member.

In another example, a medical device for occluding the left atrial appendage may comprise an expandable member including an inner layer and an outer layer and having a first end region, a second end region, and an inflation cavity, at least one fixation member having a first end and a second end coupled to the expandable member, the at least one fixation member configured to move from a delivery configuration to a deployed configuration in response to an expansion of the expandable member, and a valve member extending at least partially into the inflation cavity. The expandable member may be configured to expand and seal the opening of the left atrial appendage. Alternatively or additionally to any of the examples above, in another example, the at least one fixation member may extend radially from the inner layer towards the second layer.

Alternatively or additionally to any of the examples above, in another example, the outer layer may include at least one aperture extending from an inner surface to an outer surface of the outer layer.

Alternatively or additionally to any of the examples above, in another example, the at least one fixation member may be configured to extend through the at least one aperture in the outer layer when the at least one fixation member is in the deployed configuration.

The above summary of some embodiments is not intended to describe each disclosed embodiment or every implementation of the present disclosure. The Figures, and Detailed Description, which follow, more particularly exemplify these embodiments

BRIEF DESCRIPTION OF THE DRAWINGS

The disclosure may be more completely understood in consideration of the following detailed description of various embodiments in connection with the accompanying drawings, in which:

FIG. 8B illustrates a side view of the example occlusive implant of FIG. 8A in a deployed configuration;

Figure 1:
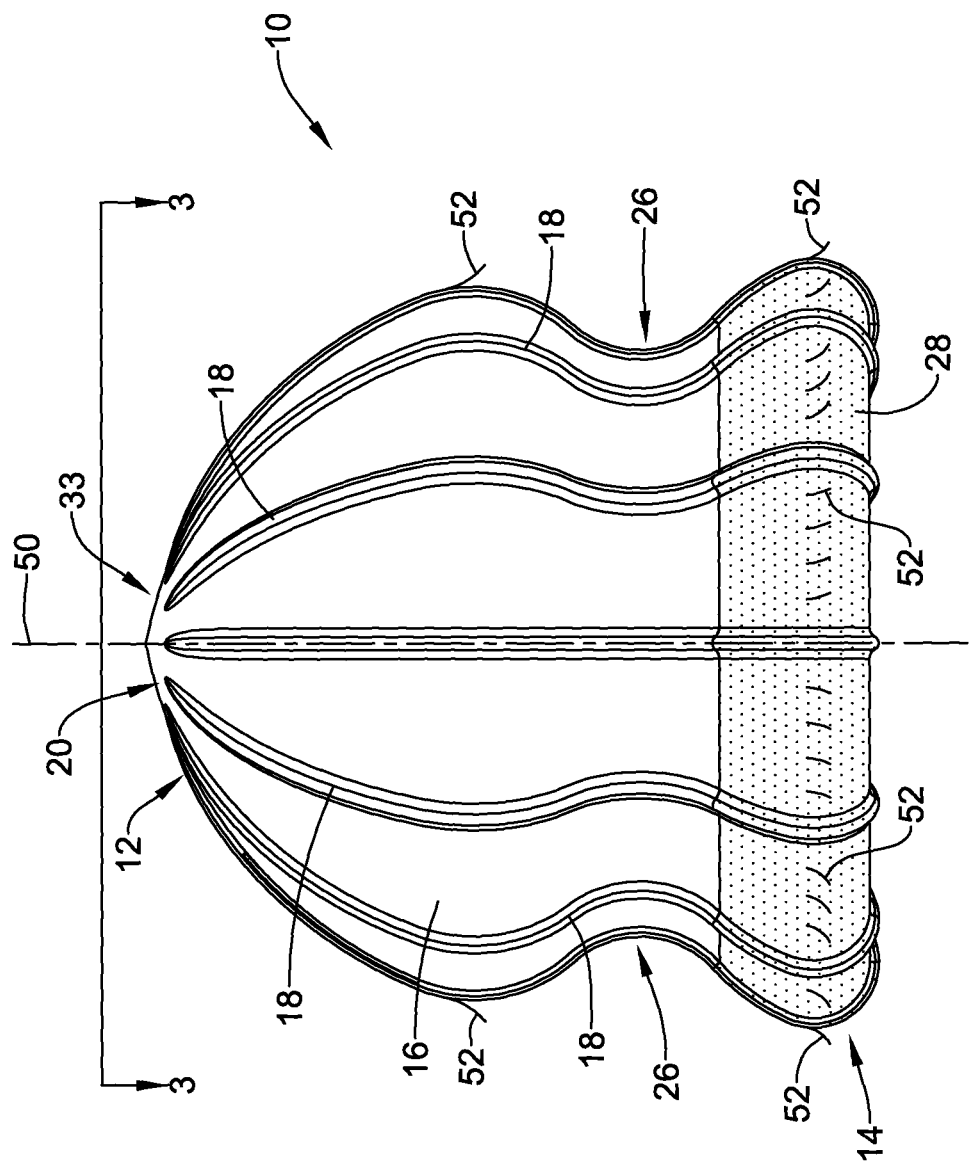
FIG. 1 is a plan view of an example occlusive implant.

While aspects of the disclosure are amenable to various modifications and alternative forms, specifics thereof have been shown by way of example in the drawings and will be described in detail. It should be understood, however, that the intention is not to limit aspects of the disclosure to the particular embodiments described. On the contrary, the intention is to cover all modifications, equivalents, and alternatives falling within the spirit and scope of the disclosure.

DETAILED DESCRIPTION

The following description should be read with reference to the drawings, which are not necessarily to scale, wherein like reference numerals indicate like elements throughout the several views. The detailed description and drawings are intended to illustrate but not limit the claimed disclosure. Those skilled in the art will recognize that the various elements described and/or shown may be arranged in various combinations and configurations without departing from the scope of the disclosure. The detailed description and drawings illustrate example embodiments of the claimed disclosure. However, in the interest of clarity and ease of understanding, while every feature and/or element may not be shown in each drawing, the feature(s) and/or element(s) may be understood to be present regardless, unless otherwise specified.

For the following defined terms, these definitions shall be applied, unless a different definition is given in the claims or elsewhere in this specification.

All numeric values are herein assumed to be modified by the term "about," whether or not explicitly indicated. The term "about", in the context of numeric values, generally refers to a range of numbers that one of skill in the art would consider equivalent to the recited value (e.g., having the same function or result). In many instances, the term "about" may include numbers that are rounded to the nearest significant figure. Other uses of the term "about" (e.g., in a context other than numeric values) may be assumed to have their ordinary and customary definition(s), as understood from and consistent with the context of the specification, unless otherwise specified.

The recitation of numerical ranges by endpoints includes all numbers within that range, including the endpoints (e.g., 1 to 5 includes 1, 1.5, 2, 2.75, 3, 3.80, 4, and 5).

Although some suitable dimensions, ranges, and/or values pertaining to various components, features and/or specifications are disclosed, one of skill in the art, incited by the present disclosure, would understand desired dimensions, ranges, and/or values may deviate from those expressly disclosed.

As used in this specification and the appended claims, the singular forms "a", "an", and "the" include plural referents unless the content clearly dictates otherwise. As used in this specification and the appended claims, the term "or" is generally employed in its sense including "and/or" unless the content clearly dictates otherwise. It is to be noted that in order to facilitate understanding, certain features of the disclosure may be described in the singular, even though those features may be plural or recurring within the disclosed embodiment(s). Each instance of the features may include and/or be encompassed by the singular disclosure(s), unless expressly stated to the contrary. For simplicity and clarity purposes, not all elements of the disclosure are necessarily shown in each figure or discussed in detail below. However, it will be understood that the following discussion may apply equally to any and/or all of the components for which there are more than one, unless explicitly stated to the contrary. Additionally, not all instances of some elements or features may be shown in each figure for clarity.

Relative terms such as "proximal", "distal", "advance", "retract", variants thereof, and the like, may be generally considered with respect to the positioning, direction, and/or operation of various elements relative to a user/operator/manipulator of the device, wherein "proximal" and "retract" indicate or refer to closer to or toward the user and "distal" and "advance" indicate or refer to farther from or away from the user. In some instances, the terms "proximal" and "distal" may be arbitrarily assigned in an effort to facilitate understanding of the disclosure, and such instances will be readily apparent to the skilled artisan. Other relative terms, such as "upstream", "downstream", "inflow", and "outflow" refer to a direction of fluid flow within a lumen, such as a body lumen, a blood vessel, or within a device.

The term "extent" may be understood to mean a greatest measurement of a stated or identified dimension, unless the extent or dimension in question is preceded by or identified as a "minimum", which may be understood to mean a smallest measurement of the stated or identified dimension. For example, "outer extent" may be understood to mean a maximum outer dimension, "radial extent" may be understood to mean a maximum radial dimension, "longitudinal extent" may be understood to mean a maximum longitudinal dimension, etc. Each instance of an "extent" may be different (e.g., axial, longitudinal, lateral, radial, circumferential, etc.) and will be apparent to the skilled person from the context of the individual usage. Generally, an "extent" may be considered a greatest possible dimension measured according to the intended usage, while a "minimum extent" may be considered a smallest possible dimension measured according to the intended usage. In some instances, an "extent" may generally be measured orthogonally within a plane and/or cross-section, but may be, as will be apparent from the particular context, measured differently—such as, but not limited to, angularly, radially, circumferentially (e.g., along an arc), etc.

The terms "monolithic" and "unitary" shall generally refer to an element or elements made from or consisting of a single structure or base unit/element. A monolithic and/or unitary element shall exclude structure and/or features made by assembling or otherwise joining multiple discrete elements together.

It is noted that references in the specification to "an embodiment", "some embodiments", "other embodiments", etc., indicate that the embodiment(s) described may include a particular feature, structure, or characteristic, but every embodiment may not necessarily include the particular feature, structure, or characteristic. Moreover, such phrases are not necessarily referring to the same embodiment. Further, when a particular feature, structure, or characteristic is described in connection with an embodiment, it would be within the knowledge of one skilled in the art to effect the particular feature, structure, or characteristic in connection with other embodiments, whether or not explicitly described, unless clearly stated to the contrary. That is, the various individual elements described below, even if not explicitly shown in a particular combination, are nevertheless contemplated as being combinable or arrangeable with each other to form other additional embodiments or to complement and/or enrich the described embodiment(s), as would be understood by one of ordinary skill in the art.

For the purpose of clarity, certain identifying numerical nomenclature (e.g., first, second, third, fourth, etc.) may be used throughout the description and/or claims to name and/or differentiate between various described and/or claimed features. It is to be understood that the numerical nomenclature is not intended to be limiting and is exemplary only. In some embodiments, alterations of and deviations from previously-used numerical nomenclature may be made in the interest of brevity and clarity. That is, a feature identified as a "first" element may later be referred to as a "second" element, a "third" element, etc. or may be omitted entirely, and/or a different feature may be referred to as the "first" element. The meaning and/or designation in each instance will be apparent to the skilled practitioner.

The occurrence of thrombi in the left atrial appendage (LAA) during atrial fibrillation may be due to stagnancy of blood pooling in the LAA. The pooled blood may still be pulled out of the left atrium by the left ventricle, however less effectively due to the irregular contraction of the left atrium caused by atrial fibrillation. Therefore, instead of an active support of the blood flow by a contracting left atrium and left atrial appendage, filling of the left ventricle may depend primarily or solely on the suction effect created by the left ventricle. However, the contraction of the left atrial appendage may not be in sync with the cycle of the left ventricle. For example, contraction of the left atrial appendage may be out of phase up to 180 degrees with the left ventricle, which may create significant resistance to the desired flow of blood. Further still, most left atrial appendage geometries are complex and highly variable, with large irregular surface areas and a narrow ostium or opening compared to the depth of the left atrial appendage. These aspects as well as others, taken individually or in various combinations, may lead to high flow resistance of blood out of the left atrial appendage.

In an effort to reduce the occurrence of thrombi formation within the left atrial appendage and prevent thrombi from entering the blood stream from within the left atrial appendage, it may be desirable to develop medical devices and/or occlusive implants that close off the left atrial appendage from the heart and/or circulatory system, thereby lowering the risk of stroke due to thromboembolic material entering the blood stream from the left atrial appendage. Example medical devices and/or occlusive implants that close off the left atrial appendage are disclosed herein.

FIG. 1 illustrates an example occlusive implant 10. The occlusive implant 10 may include a first end region 12 and a second end region 14. As will be discussed in greater detail herein, the first end region 12 may include the portion of the occlusive implant 10 which extends farthest into a left atrial appendage, while the second end region 14 may include the portion of the occlusive implant 10 which is positioned closer to an opening of the left atrial appendage.

The occlusive implant 10 may include an expandable member 16. The expandable member 16 may also be referred to as an expandable balloon 16. The expandable member 16 may be formed from a highly compliant material which permits the expandable member 16 to expand from a first unexpanded (e.g., deflated, collapsed, delivery) configuration to a second expanded (e.g., inflated, delivered) configuration with an inflation material or inflation media. In some examples, the expandable balloon 16 may be inflated to pressures from about 4 pounds per square inch (psi) to about 200 psi. It can be appreciated that the outer diameter of the implant 10 may be larger in the expanded configuration versus the unexpanded configuration. Example materials used for the inflation material may be hydrogel beads (or other semi-solid materials), thermoreversible copolymer, saline, etc.

In some examples, the inflatable member 16 may be constructed from silicone or a low-durometer polymer, however, other materials are contemplated. Additionally, the expandable member 16 may be impermeable to blood and/or other fluids, such as water. In some embodiments, the expandable member 16 may include a woven, braided and/or knitted material, a fiber, a sheet-like material, a metallic or polymeric mesh, or other suitable construction. Further, in some embodiments, the expandable member 16 may prevent thrombi (e.g., blood clots, etc.) originating in the left atrial appendage from passing through the occlusive device 10 and into the blood stream. In some embodiments, the occlusive device 10 may promote endothelial growth after implantation, thereby effectively removing the left atrial appendage from the patient's circulatory system. Some suitable, but non-limiting, examples of materials for the occlusive member 10 are discussed below.

Figure 2:
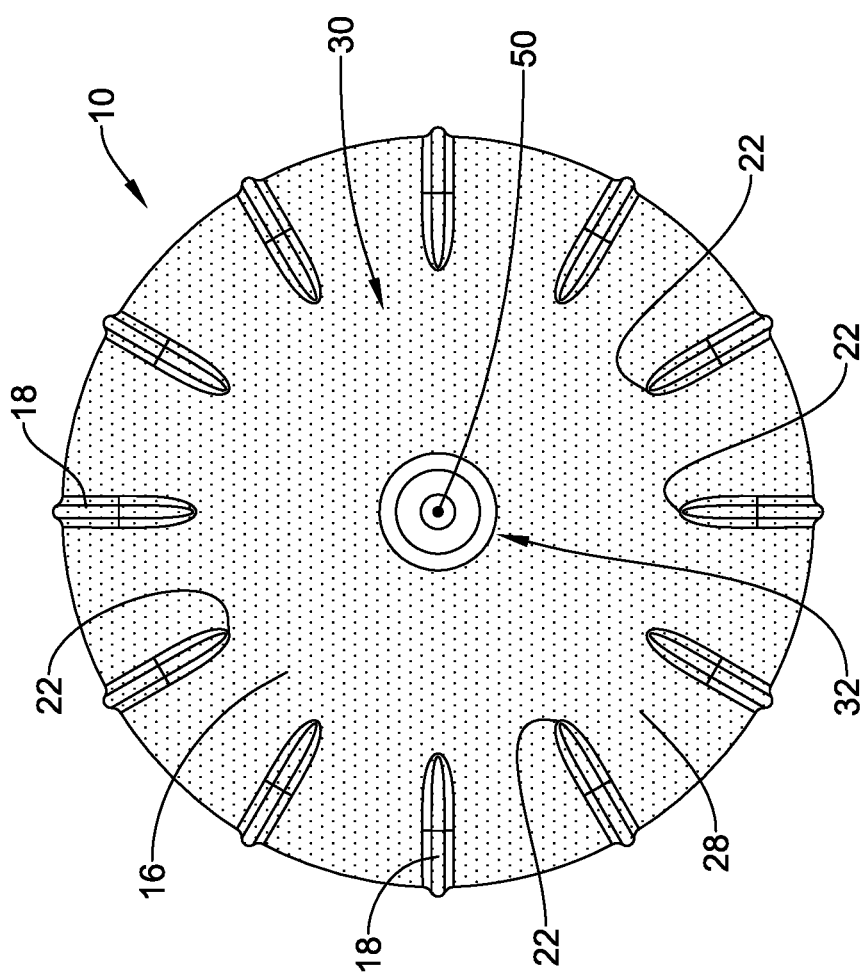
FIG. 2 illustrates a bottom view of the example occlusive implant shown in FIG. 1.

FIG. 1 further illustrates that occlusive member 10 may include one or more spine members 18 extending along the longitudinal axis 50 of the expandable member 16 from the second end region 14 to the first end region 12. In some examples described herein, the spine members 18 may be described as positioning members 18. Each of the spine members 18 may include a first end 20 and a second end 22 (the second end 22 is shown in FIG. 2). FIG. 1 further illustrates that each of the individual spine members 18 may be spaced apart from adjacent spine members 18. In other words, the spacing between adjacent spine members 18 may be substantially uniform around the circumference of the expandable member 16. In some examples, the spine members 18 may include one or more materials which are stiffer, higher durometer materials than the material utilized to construct the expandable member 16. Some suitable, but non-limiting, examples of materials for the spine members 18 are discussed below.

Further, it is contemplated that in some instances the spacing between spine members 18 may not be uniform. In some examples, the spacing between adjacent spine members 18 may be variable (e.g., non-uniformly spaced) around the circumference of the expandable member 16. Additionally, it is contemplated that the spine member 18 may form a framework in which the spine members 18 are connected to one another via a series of laterally extending members. A variety of different geometries for example frameworks are contemplated.

As illustrated in FIG. 1, the first end region 12 of the expandable member 16 may extend radially inward to form an apex region 33. Additionally, as shown in FIG. 1, each of the first end portions 20 of each of the spine members 18 may extend inward along the longitudinal axis 50 toward the apex region 33 of the expandable member 16.

Additionally, FIG. 1 illustrates that the occlusive member 10 may include a "nesting region" 26. The nesting region 26 may define a portion of the occlusive member 10 which is configured to nest within an opening of the left atrial appendage (as will be illustrated and described further in FIG. 14). The nesting region 26 may include a portion of the occlusive member 10 which extends radially inward toward the longitudinal axis 50 of the occlusive member 10. Further, the inward curve which defines the nesting region 26 may extend circumferentially around the occlusive member 10. In other words, the inward curvature of the nesting region 26 may resemble a channel or groove which extends around the circumference of the occlusive member 10.

FIG. 1 further illustrates that the second end region 14 of the occlusive member 10 may include a coating 28. The coating 28 may extend around the circumference of the occlusive member 10 (including both the expandable member 16 and the spine members 18). In some examples, the coating 28 may promote cellular growth along the surface thereof. For example, the coating 28 may include elements which promote endothelial growth along the surface thereof. For example, the endothelial growth elements may accelerate the ability for endothelial cellular tissue to form a seal across an opening of the left atrial appendage. In other examples, the coating 28 may include a polymer mesh (e.g., PET mesh), a woven, braided and/or knitted material, a fiber, a sheet-like material, a metallic or polymeric mesh, or other similar materials which may be coupled to the outer surface of the expandable member 16.

FIG. 1 further illustrates that the expandable member 16 may include one or more fixation members 52. The fixation members 52 may include, barbs, hooks, surface texture, bristles, etc. configured to extend into and/or otherwise engage tissue disposed adjacent to the expandable member 16 (when implanted within the body. The fixation member 52 may be configured to be safely constrained while the occlusive member 10 is delivered to the desired implant location and subsequently activated or moved to a deployed configuration. In some instances, as will be described in more detail herein, the changing shape of the expandable member 16 as it is inflated may deploy the one or more fixation members 52. For example, as the expandable member 16 transforms (e.g., is inflated) from a collapsed or constrained (e.g., unexpanded or deflated) configuration to an expanded or inflated configuration, the expandable member 16 may undergo or experience surface stretching, distension, elongation, pressure changes, etc. It is contemplated that any of these changing features may be used to cause the deployment of or a change in the shape of the fixation members 52, as will be described in more detail herein.

The fixation members 52 may be spaced from one another about a length and/or circumference of the expandable member 16, as desired. The longitudinal spacing and/or the circumferential spacing between the fixation members 52 may be substantially uniform. However, it is contemplated that the longitudinal spacing and/or the circumferential spacing between the fixation members 52 may not be uniform. In some examples, the longitudinal spacing and/or the circumferential spacing between the fixation members 52 may be variable. Further, there may be any number of fixation members 52 desired, such as, but not limited to, 0, 1, 2, 3, 4, 5, 6, 7, 8, 9, 10, 11, 12, 13, 14, 15, 16 or more.

FIG. 2 illustrates a bottom view of the occlusive device described in FIG. 1. FIG. 2 illustrates that the occlusive device may include a bottom surface 30. As discussed above, the second end regions 22 of the spine members 18 may "wrap" along (e.g., around) the second end region 14 (shown in FIG. 1) and terminate along the bottom surface 30.

FIG. 2 further shows twelve spine members 18 positioned circumferentially around the longitudinal axis 50 of the occlusive device 10. However, while FIG. 2 illustrates twelve spine members 18 positioned around the longitudinal axis 50 of the occlusive device 10, it is contemplated that greater than or less than twelve spine members 18 may be utilized for any example occlusive devices 10 contemplated herein. For example, occlusive device 10 may include 0, 1, 2, 3, 4, 5, 6, 7, 8, 9, 10, 11, 12, 13, 14, 15, 16 or more spine members 18 positioned along the occlusive device 10.

As will be described in greater detail herein, FIG. 2 further illustrates a valve member 32 positioned in a central region of the bottom surface 30 of the occlusive member 10. The valve 32 may be utilized as an access aperture to insert a secondary medical device (not shown). The secondary medical device may be utilized to inject a fluid material into the expandable member 16. FIG. 2 further illustrates that the coating 28 may be positioned along the bottom surface 30 of the occlusive device 10. The coating 28 may cover all or a portion of the bottom surface 30 of the occlusive device 10.

Figure 3:
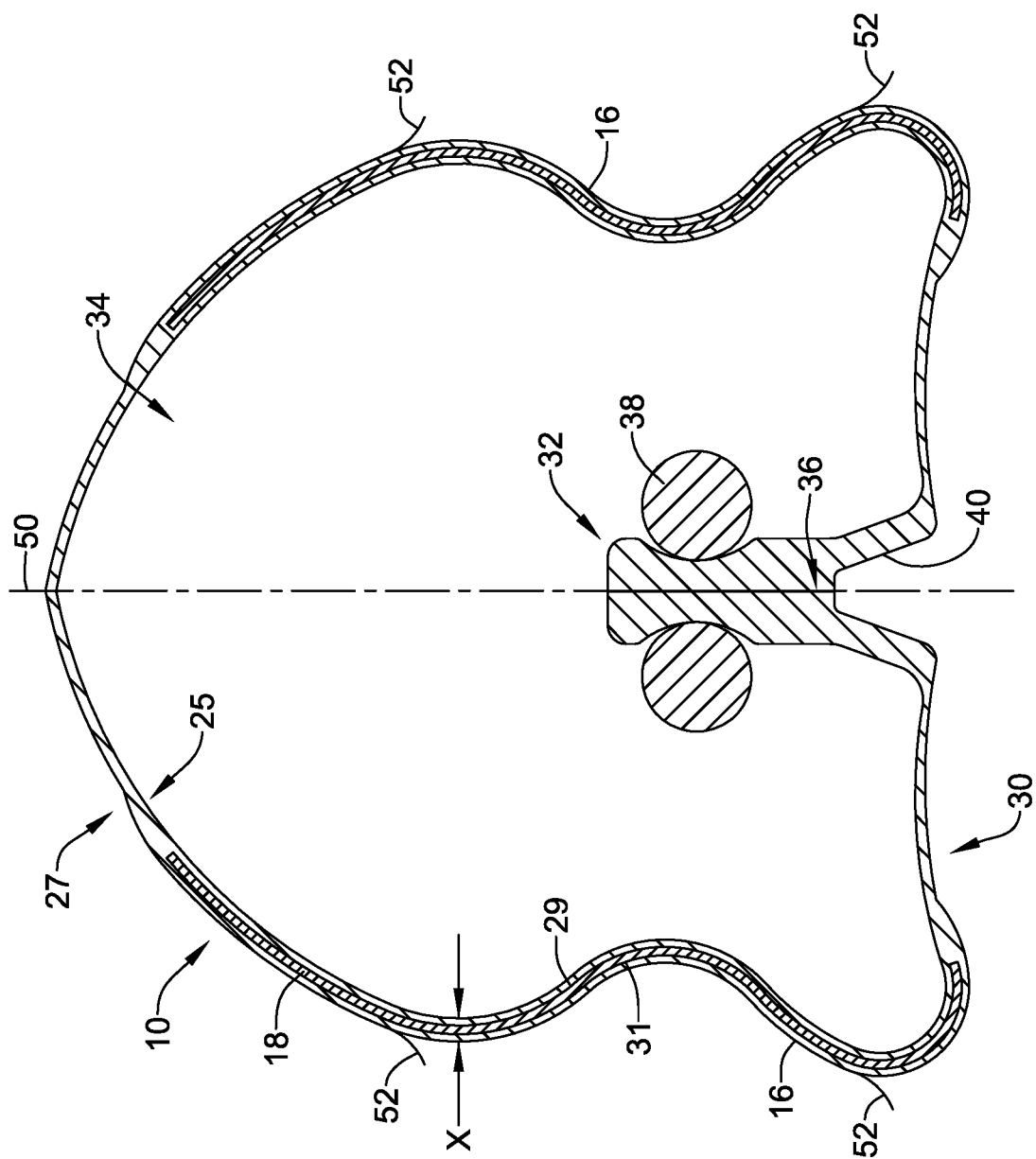
FIG. 3 illustrates a cross-sectional view along line 3-3 of FIG. 1.

FIG. 3 shows a cross-sectional view along line 3-3 of FIG. 1. FIG. 3 illustrates that the expandable member 16 may include an inner surface 25 and outer surface 27. Additionally, FIG. 3 shows that the expandable member 16 may include a wall thickness "X" defined as the width of the wall between the inner surface 25 and outer surface 27 of the expandable member 16.

FIG. 3 further illustrates that the spine members 18 may be positioned within the wall of the expandable member 16. FIG. 3 illustrates that each of the spine members 18 may include an inwardly-facing surface 29 and an outwardly-facing surface 31. The inner surface 29 of each of the spine members 18 may be positioned radially outward of the inner surface 25 of the expandable member 16. Further, the outer surface 31 of each of the spine members 18 may be positioned radially inward of the outer surface 27 of the occlusive member 10. In other words, each of the spine members 18 be embedded (e.g., encased, surrounded, etc.) within the wall of the expandable member 16. However, this is not intended to be limiting. Rather, it can be appreciated that in some examples, a portion of one or more of the spine members 18 may extend radially away from the outer surface 27 of the expandable member 16. For example, in some instances a portion of the outer surface 31 of one or more of the spine members 18 may be free from the expandable member 16.

FIG. 3 further illustrates that the expandable member 16 may include an inner cavity 34. Inner cavity 34 may be described as a chamber in which an inflation media (for example, but not limited to, hydrogel beads, semi-solid materials, saline or other suitable liquids, gases, etc.) may be injected (via valve 32, for example) in order to expand the expandable member 16. As will be described in greater detail herein, as an inflation media is inserted into the expandable member 16, the inner cavity 34 may expand, thereby permitting the expandable member 16 to seal against the tissue walls defining an opening in the left atrial appendage.

As stated above, inflation of the inner cavity 34 may be accomplished by inserting inflation media through the valve 32. As shown in FIG. 3, the valve 32 may be formed from the same material that forms the wall of the expandable member 16. In other words, the valve 32 may be an extension of the wall of the expandable member 16. Additionally, as illustrated in FIG. 3, the valve 32 may be positioned within the inner cavity 34. For example, FIG. 3 illustrates that the valve 32 may extend (e.g., project) into the inner cavity 34 from the bottom surface 30.

The valve 32 may include an inflation lumen 36 which may be designed to allow a secondary medical device to be inserted therethrough. As shown in FIG. 3, the inflation lumen 36 may be aligned with the longitudinal axis 50 of the occlusive member 10. FIG. 3 shows the inflation lumen 36 in a closed configuration such that it would prevent inflation media (not shown in FIG. 3) from passing back through the valve 32. As shown in FIG. 3, in some examples the valve 32 may be maintained in a closed configuration via a torus-shaped mechanical gasket 38. For simplicity purposes, the gasket 38 may be referred to as an "O-ring" in the remaining discussion. It is contemplated that other sealing mechanisms, such as, but not limited to, one way valves, may also be used to allow for inflation while retaining the inflation media within the cavity. Some illustrative sealing mechanisms are described in commonly assigned U.S. Patent Application No. 62/607,053 filed on Dec. 18, 2017 and titled "OCCLUSIVE DEVICE WITH EXPANDABLE MEMBER," the disclosure of which is hereby incorporated by reference.

It can be appreciated that the O-ring 38 may be formed from a material (e.g., rubber, elastomer, etc.) which permits it to compress radially inwardly. As shown in FIG. 3, the O-ring 38 may be positioned around the valve 32 such that the O-ring 38 compresses the lumen 36 of valve 32 shut. However, the O-ring 38 must also permit the lumen 36 to open enough for a secondary medical device to be inserted therethrough (for inflation of the expandable member 16 as described above). Therefore, in some examples the O-ring 38 may designed to stretch and allow an inflation device access to the inner chamber 34 while also exerting sufficient radially inward force to maintain the lumen 36 in a closed configuration once the inner chamber 34 has been inflated and after the inflation device (not shown in FIG. 3) is removed from the lumen 36 (inflation of the chamber 34 will be discussed with respect to FIG. 14 and FIG. 15).

As will be discussed in greater detail below, the occlusive member 10 may be coupled to a delivery system in a variety of ways. Further, a component of the delivery system may also function as a secondary medical device utilized to inflate the expandable member 16. FIG. 3 illustrates an attachment region 40 which may be utilized to attach the delivery system to the occlusive member 10. Attachment region 40 may be include a variety of features which permit attachment to a delivery system. For example, attachment region 40 may include threads which mate with a threaded region on a delivery catheter (not shown in FIG. 3). In other examples, the attachment region 40 may be designed such that it forms a "press-fit" with a distal end region of a delivery catheter. Other methods of attaching the occlusive device 10 to the delivery catheter may include a ratcheting mechanism, break-away mechanisms, detent lock, spring lock, single-piece coupling, two-piece coupling, or combinations thereof.

Figure 4A:
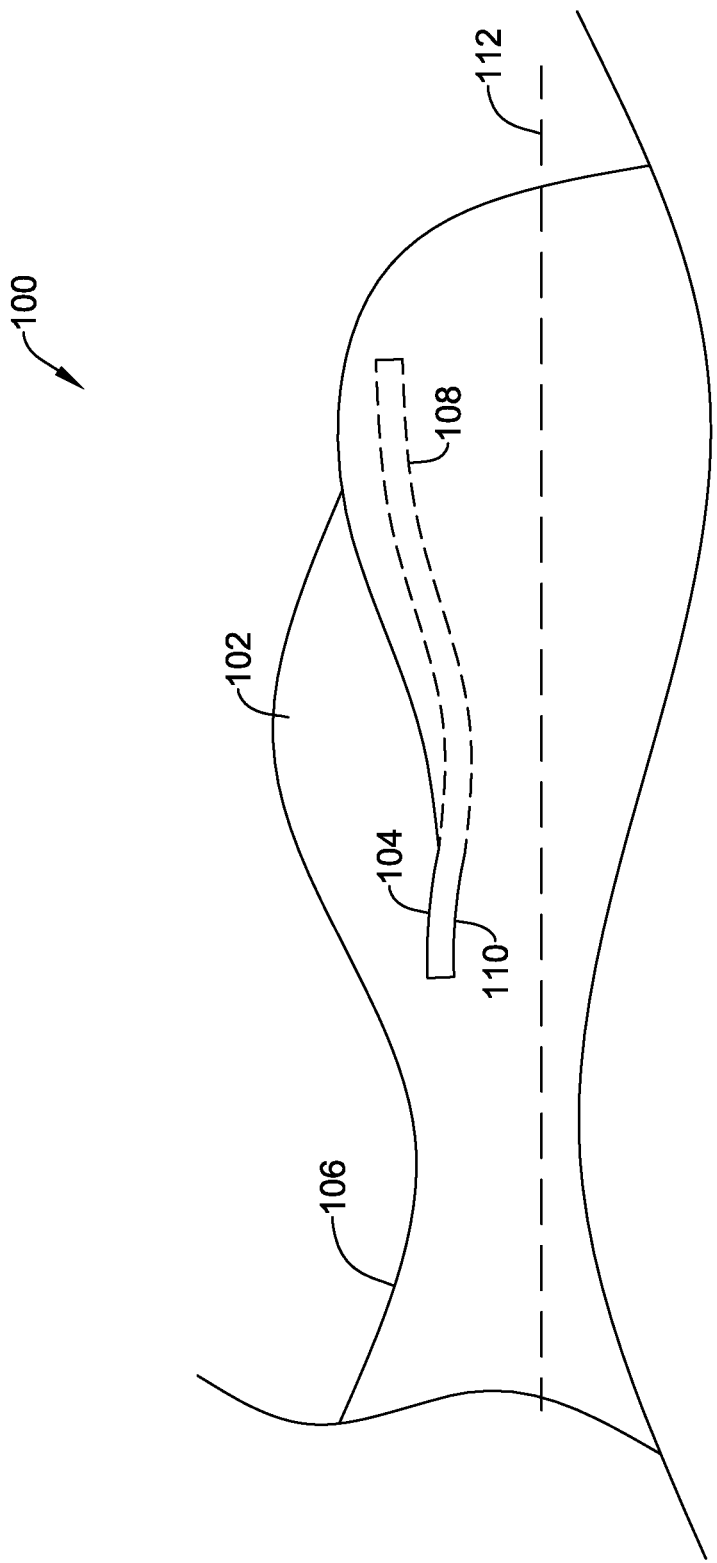
FIG. 4A illustrates a partial side view of another example occlusive implant in a delivery configuration.

FIG. 4A illustrates a partial side view of another example occlusive device 100 in a collapsed or delivery configuration. The occlusive device 100 may be similar in form and function to the occlusive device 10. For example, the occlusive device 100 may include an expandable member 102 and one or more fixation members or mechanisms 104 coupled thereto. While not explicitly shown, the expandable member 102 may include an inner cavity configured to receive an inflation fluid to expand the occlusive device from the collapsed delivery configuration to an expanded deployed configuration (as shown in FIG. 4C).

FIG. 4A illustrates a single fixation member 104, however, it is contemplated that the occlusive device 100 may include any number of fixation members 104 distributed about the length and/or circumference, as desired. The one or more fixation members 104 may be coupled to an outer surface 106 of the expandable member 102. It is contemplated that the fixation member 104 may be secured using an adhesive, heat bonding, molding, or other techniques, as desired. It is contemplated that the one or more fixation members 104 may be secured to the expandable member 102 along less than an entire length of the fixation member 104. This may allow at least a portion of the fixation member 104 to extend radially away from an outer surface 106 of the expandable member 102 as the expandable member 102 is inflated. The fixation member 104 made be formed from a metal (e.g., stainless steel), a composite, a shape memory material (e.g., Nitinol), a polymer (e.g., polyester, etc.) or combinations thereof.

As shown in FIG. 4A, the fixation member 104 may have one or more bends or curved portions 108 positioned along a length thereof. The bends 108 may be positioned along the length such that when the occlusive device 100 is in the collapsed configured (as shown in FIG. 4A), a first end 110 of the fixation member 104 configured to be deployed into a body tissue extends parallel to or approximately parallel to a longitudinal axis 112 of the expandable member 102. While not explicitly shown, in some embodiments, the fixation member 104 may be configured to extend radially about the expandable member 102 or at a non-parallel angle relative to the longitudinal axis 112. In some cases, the expandable member 102 may be folded over the fixation member 104 during delivery of the occlusive member 100 such that the fixation member 104 is covered and prevented from inadvertently engaging tissues, although this is not required. In other examples, the fixation member 104 may be covered with a sheathing member (not explicitly shown) during delivery of the occlusive member 100. In yet another embodiment, the fixation member 104 may be positioned between two layers of a multi-walled balloon. In such embodiments, the fixation member 104 may be configured to exit the outer layer upon expansion of the expandable member 102 through a preformed aperture or by puncturing a hole through the outermost layer. It is contemplated that the innermost layer may provide a fluid-tight seal such that inflation fluid remains within the inflation cavity.

Figure 4B:
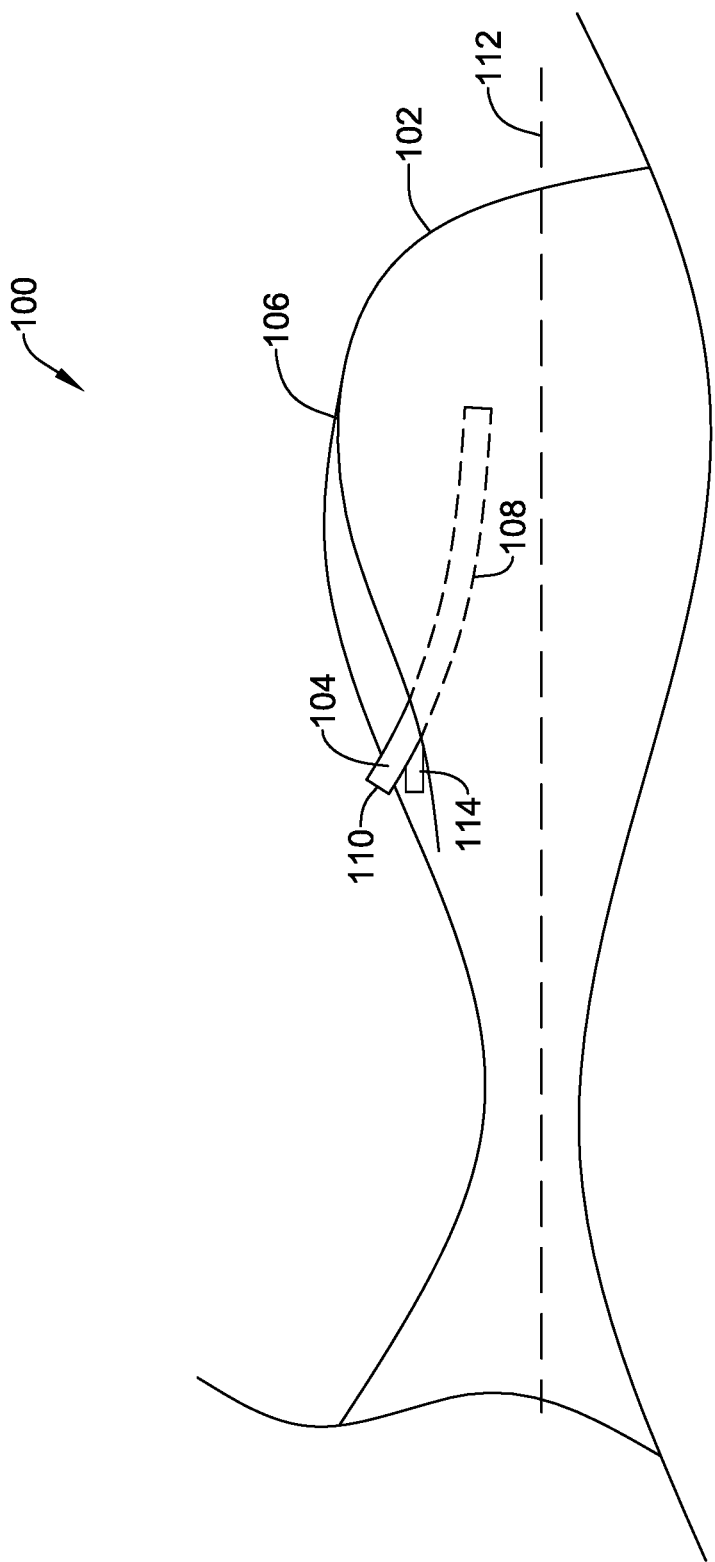
FIG. 4B illustrates a partial side view of the example occlusive implant of FIG. 4A in a partially expanded configuration.
Figure 4C:
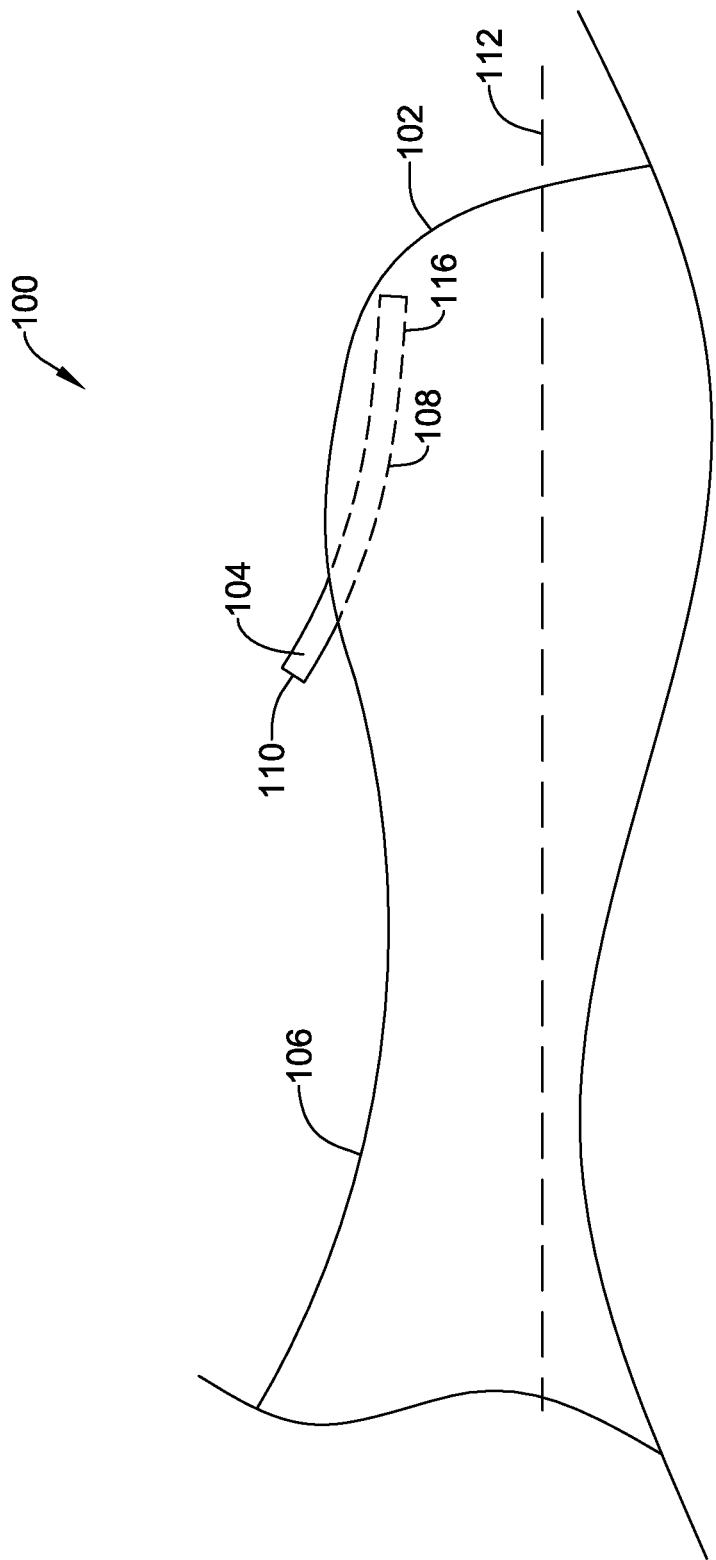
FIG. 4C illustrates a partial side view of the example occlusive implant of FIG. 4A in an expanded configuration.

As the occlusive device 100 is inflated or expanded, the shape of the expandable member 102 may begin to change, as shown in FIG. 4B. As the pressure increases within the inflation cavity, the expandable member 102 begins to assume its expanded shape. In some instances, as the expandable member 102 is inflated, the outer surface 106 of the expandable member 102 assumes a curved profile. As the outer surface 106 changes shape, the first end 110 of the fixation member 104 is moved away from a generally parallel configuration. For example, the shape of the outer surface 106 of the expandable member 102 and the shape of the bends 108 may be such that the first end 110 of the fixation member 104 extends at a non-parallel angle to the longitudinal axis 112. In some cases, the outer surface 106 of the expandable member 102 may include one or more channels or recesses 114 configured to receive the one or more fixation members 104, although this is not required. When so provided, the one or more channels 114 may be molded into the shape of the expandable member 102. In other embodiments, the one or more channels 114 may be adhered or other coupled to or into the wall of the expandable member 102. For example a tubular member defining a channel 114 may be bonded, overmolded, sutured, etc. to the expandable member 102.

As the occlusive device 100 is inflated or expanded beyond the partially inflated configuration shown in FIG. 4C, the shape of the expandable member 102 continues to change until it reaches the fully expanded configuration, as shown in FIG. 4C. Depending on the compliance of the expandable member 102, in some cases, the expandable member 102 may be inflated beyond a fully expanded configuration (e.g., overinflated) and will continue to change shape as long as inflation fluid is added to the internal cavity. In some instances, as the expandable member 102 reaches its expanded configuration, the outer surface 106 of the expandable member 102 assumes a more curved profile (e.g., more so than in the partially inflated configuration). As the outer surface 106 changes shape, the first end 110 of the fixation member 104 is moved further away from the generally parallel configuration shown in FIG. 4A while a second end 116 of the fixation member 104 remains in contact with the outer surface 106 of the expandable member 102. For example, the shape of the outer surface 106 of the expandable member 102 and the shape of the bends 108 may be such that the first end 110 of the fixation member 104 extends at a non-parallel angle to the longitudinal axis 112. In some cases, in the expanded configuration the first end 110 of the fixation member 104 may have a non-parallel angle that is greater than the non-parallel angle of the partially inflated configuration (e.g., FIG. 4B), although this is not required. As the expandable member 102 is inflated, the first end 110 of the fixation member 104 is moved towards and driven into adjacent tissue to help secure the occlusive device 100 within the LAA.

It is contemplated that if it is desired to remove and/or reposition the occlusive device 100, the inflation fluid may be partially or fully evacuated from the inflation cavity. As the inflation fluid is removed, the expandable member 102 may collapse or reduce in size. The first end 110 fixation member 104 may disengage from the tissue and moved towards the generally parallel configuration illustrated in FIG. 4A. This may allow the occlusive device 100 to be repositionable and/or recapturable, if so desired.

Figure 5A:
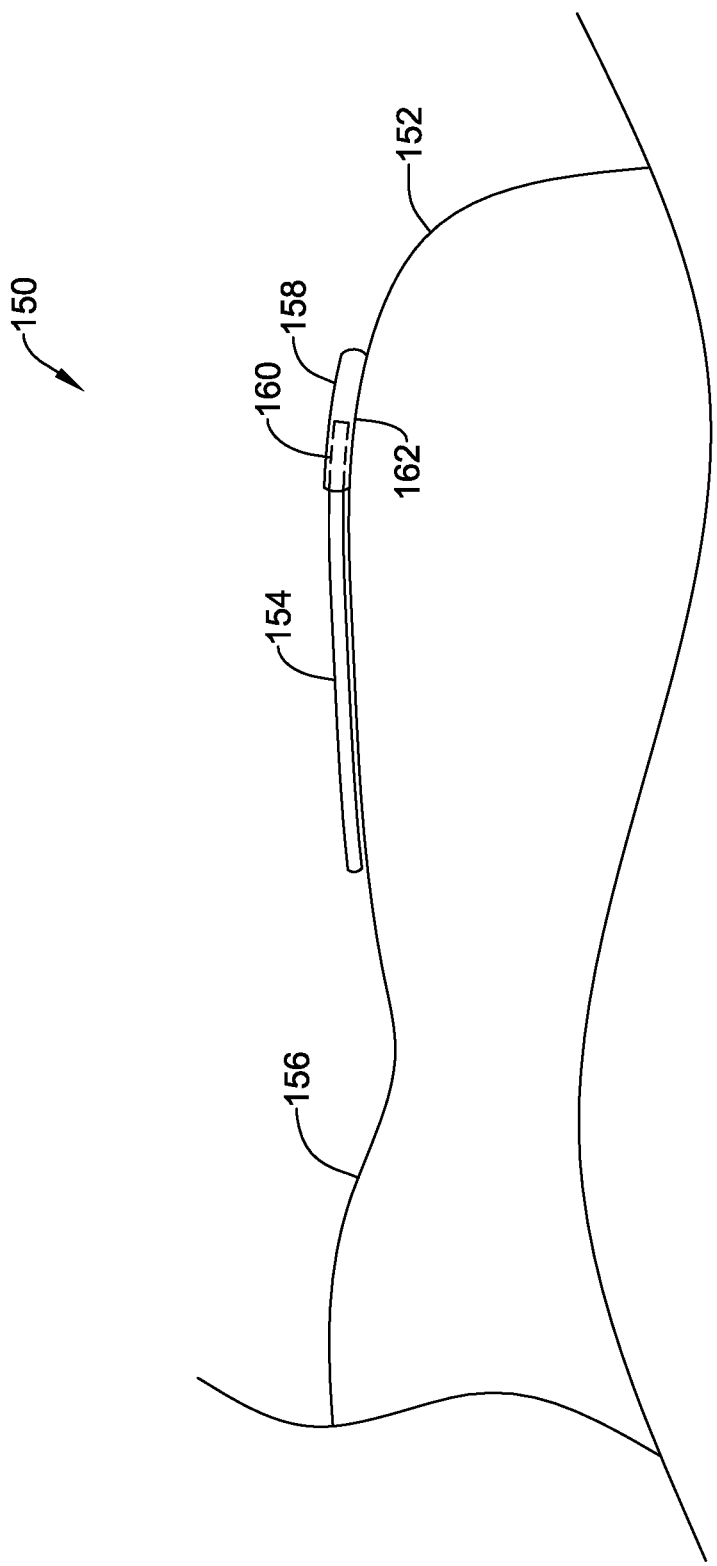
FIG. 5A illustrates a partial side view of another example occlusive implant in a delivery configuration.
Figure 5B:
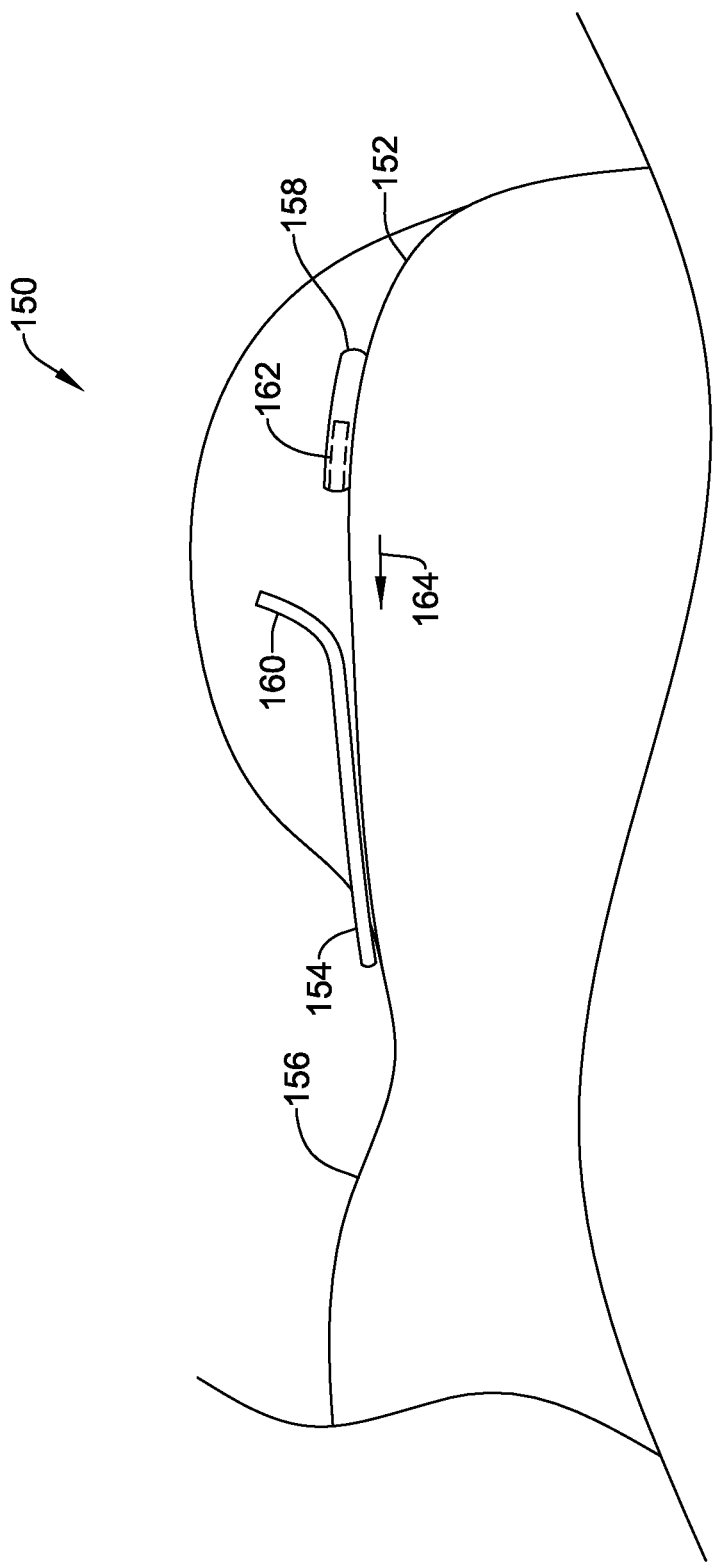
FIG. 5B illustrates a partial side view of the example occlusive implant of FIG. 5A in a deployed configuration.

FIG. 5A illustrates a partial side view of another example occlusive device 150 in a collapsed or delivery configuration. The occlusive device 150 may be similar in form and function to the occlusive device 10. For example, the occlusive device 150 may include an expandable member 152 and one or more fixation members or mechanisms 154 coupled thereto. While not explicitly shown, the expandable member 152 may include an inner cavity configured to receive an inflation fluid to expand the occlusive device from the collapsed delivery configuration to an expanded deployed configuration (as shown in FIG. 5B).

FIG. 5A illustrates a single fixation member 154, however, it is contemplated that the occlusive device 150 may include any number of fixation members 154 distributed about the length and/or circumference, as desired. The one or more fixation members 154 may be coupled to an outer surface 156 of the expandable member 152. It is contemplated that the fixation member 154 may be secured using an adhesive, heat bonding, molding, or other techniques, as desired. It is contemplated that the one or more fixation members 154 may be secured to the expandable member 152 along less than an entire length of the fixation member 154. This may allow at least a portion of the fixation member 154 to extend radially away from an outer surface 156 of the expandable member 152 as the expandable member 152 is inflated. The fixation member 154 made be formed from a metal (e.g., stainless steel), a composite, a shape memory material (e.g., Nitinol), a polymer (e.g., polyester, etc.) or combinations thereof.

As shown in FIG. 5A, a first end 160 of the fixation member 154 may extend into a sheathing element 158. The sheathing element 158 may have a lumen or cavity 162 configured to receive the first end of the fixation member 154 therein. In some embodiments, the sheathing element 158 and/or cavity 162 maybe embedded into the wall of the expandable member 152. For example, the sheathing element 158 and/or cavity 162 may be molded, bonded, sutured, etc. to or within the wall of the expandable member 158. It is contemplated that the first end 160 of the fixation member 154 may be pre-formed to extend radially away from the outer surface 156 of the expandable member 152. It is contemplated that sheathing element 158 may exert a biasing force on the first end 160 of the fixation member 154 to maintain the first end 160 in a collapsed delivery configuration. As the occlusive device 150 is inflated or expanded, the shape of the expandable member 152 may begin to change, as shown in FIG. 5B. As the pressure increases within the inflation cavity, the expandable member 152 begins to assume its expanded shape. In some instances, as the expandable member 152 is inflated, the outer surface 156 of the expandable member 152 assumes a curved profile. As the outer surface 156 changes shape, the first end 160 of the fixation member 154 is moved longitudinally away (e.g., by longitudinal distention) from the sheathing element 158, as shown at arrow 164. Once the first end 160 of the fixation member 154 is no longer disposed within the cavity 162 of the sheathing element 158, the first end 160 resumes its preformed state, as shown in FIG. 5B. The pre-formed state may be such that the first end 160 is directed radially away from the expandable member 152 and towards a body tissue. As the expandable member 152 is inflated, the first end 160 of the fixation member 154 is moved towards and driven into adjacent tissue (once free from the sheathing element 158) to help secure the occlusive device 150 within the LAA. It is contemplated that while the fixation member 154 and sheathing element 158 are described as mounted and movable longitudinally, the fixation member 154 and sheathing element 158 may be mounted such that radial distention deploys the first end 160 of the fixation member.

Figure 6A:
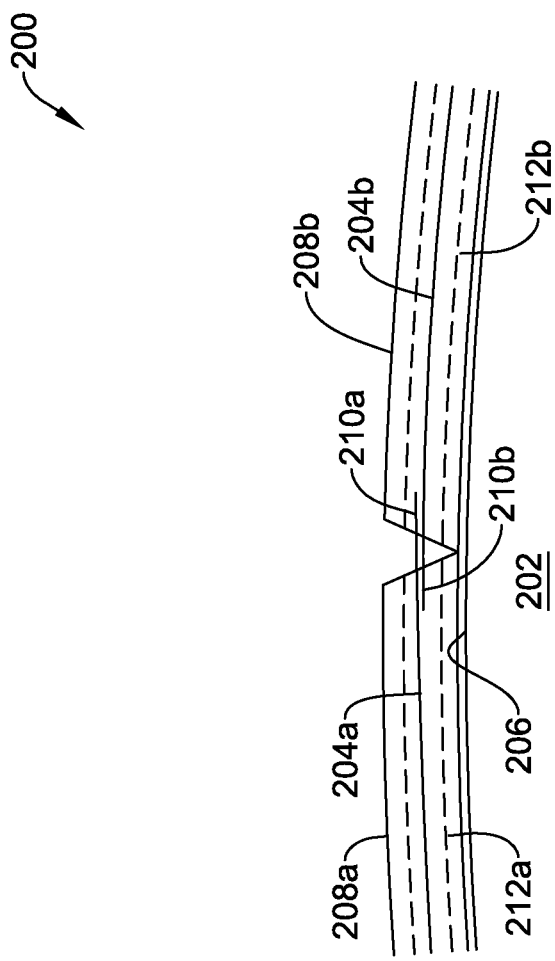
FIG. 6A illustrates a partial side view of another example occlusive implant in a delivery configuration.
Figure 6B:
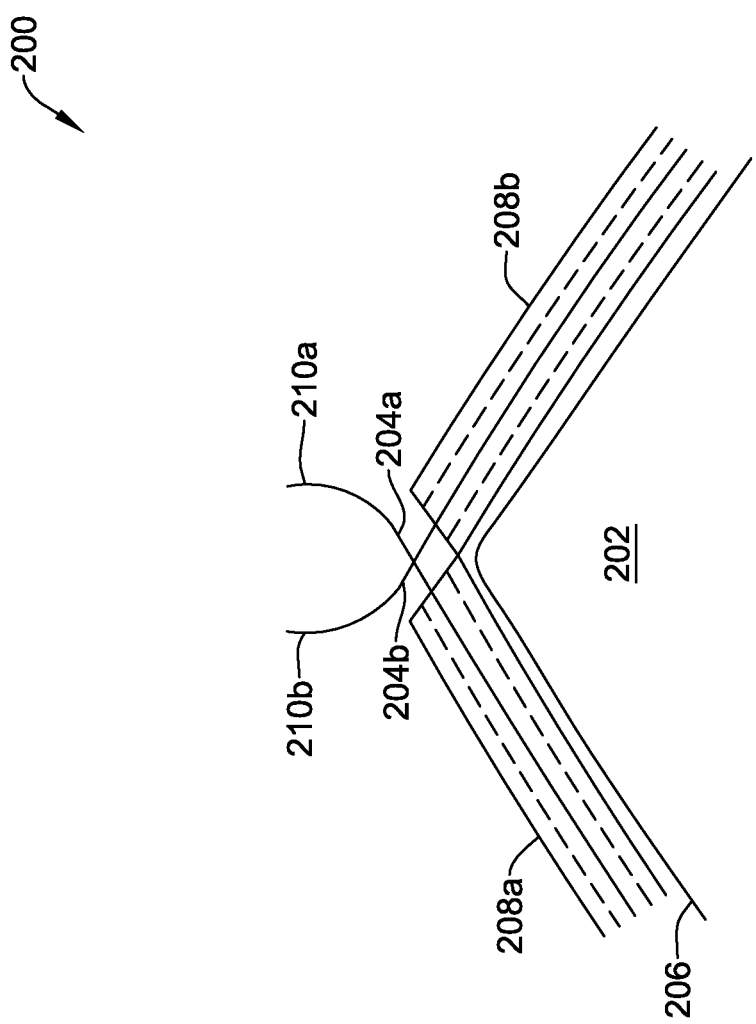
FIG. 6B illustrates a partial side view of the example occlusive implant of FIG. 6A in a deployed configuration.

FIG. 6A illustrates a partial side view of another example occlusive device 200 in a collapsed or delivery configuration. The occlusive device 200 may be similar in form and function to the occlusive device 10. For example, the occlusive device 200 may include an expandable member 202 and two or more fixation members or mechanisms 204a, 204b (collectively, 204) coupled thereto. While not explicitly shown, the expandable member 202 may include an inner cavity configured to receive an inflation fluid to expand the occlusive device from the collapsed delivery configuration to an expanded deployed configuration (as shown in FIG. 6B).

FIG. 6A illustrates two fixation members 204a, 204b, however, it is contemplated that the occlusive device 200 may include any number of fixation members 204 distributed about the length and/or circumference, as desired. The one or more fixation members 204 may be coupled to an outer surface 206 of the expandable member 202. In some instances, a first end 210a, 210b (collectively, 210) of the fixation members 204a, 204b may be unsecured while a second end (not explicitly shown may be secured to the expandable member 202. It is contemplated that the fixation members 204 may be secured using an adhesive, heat bonding, molding, or other techniques, as desired. It is contemplated that the two or more fixation members 204 may be secured to the expandable member 202 along less than an entire length of the fixation members 204. This may allow at least a portion of the fixation member 204 to extend radially away from an outer surface 206 of the expandable member 202 as the expandable member 202 is inflated. The fixation members 204 made be formed from a metal (e.g., stainless steel), a composite, a shape memory material (e.g., Nitinol), a polymer (e.g., polyester, etc.) or combinations thereof.

The occlusive device 200 may further include two or more sheathing elements 208a, 208b (collectively, 208) coupled to an outer surface 206 of the expandable member 202. The sheathing elements 208a, 208b may each include a lumen 212a, 212b (collectively, 212) extending therethrough. The lumens 212 may be configured to at least partially receive the fixation members 204. In some cases, the lumens 212 may extend an entire length of the sheathing elements 208. In other embodiments, the lumens 212 may extend for less than an entire length of the sheathing elements 208. In such an instance, the second ends of the fixation members 204 may be secured to and/or within the lumens 212. The first ends 210a, 210b of the fixation members 204 may be configured to extend to the opposition lumen when the fixation members 204 are in a delivery configuration. For example, a first fixation member 204a may be positioned within the lumen 212a of the first sheathing element 208a such that the first end 210a extends from the first lumen 212a and into the lumen 212b of the second sheathing element 208b. Similarly, the second fixation member 204b may be positioned within the lumen 212b of the second sheathing element 208b such that the first end 210b extends from the second lumen 212b and into the lumen 212a of the first sheathing element 208a.

It is contemplated that the first ends 210 of the fixation members 204 may be pre-formed to extend radially away from the outer surface 206 of the expandable member 202. It is contemplated that sheathing elements 208 may exert a biasing force on the first ends 210 of the fixation members 204 to maintain the first ends 210 in a collapsed delivery configuration. As the occlusive device 200 is inflated or expanded, the shape of the expandable member 202 may begin to change, as shown in FIG. 6B. As the pressure increases within the inflation cavity, the expandable member 202 begins to assume its expanded shape. In some instances, as the expandable member 202 is inflated, the outer surface 206 of the expandable member 202 assumes a curved profile. As the outer surface 206 changes shape, the first ends 210 of the fixation members 204 are moved longitudinally away (e.g., by longitudinal distention) from the sheathing elements 208. In other words, the as the expandable member 202 is inflated, the second ends of the fixation members 204 are drawn away from one another and the first ends 210 are withdrawn from the opposing sheathing element 208. Once the first end 210a of the first fixation member 204a is no longer disposed within the lumen 212b of the second sheathing element 208b and the first end 210b of the second fixation member 204b is no longer disposed within the lumen 212a of the first sheathing element 208a, the first ends 210 are free to resume their pre-formed state, as shown in FIG. 6B. The pre-formed state may be such that the first ends 210 are directed radially away from the expandable member 202 and towards a body tissue. As the expandable member 202 is inflated, the first ends 210 of the fixation members 204 are moved towards and driven into adjacent tissue (once free from the sheathing elements 208) to help secure the occlusive device 200 within the LAA. It is contemplated that while the fixation members 204 and sheathing elements 208 are described as mounted and movable longitudinally, the fixation members 204 and sheathing elements 208 may be mounted such that radial distention deploys the first ends 210 of the fixation members 204.

Figure 7A:
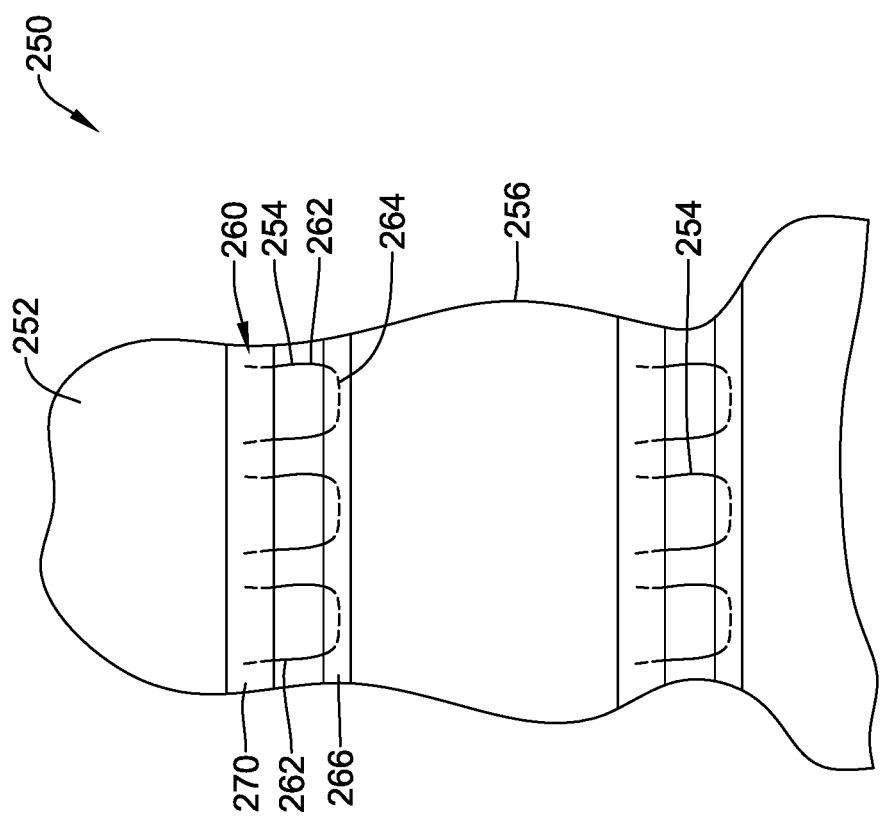
FIG. 7A illustrates a side view of another example occlusive implant in a delivery configuration.
Figure 7B:
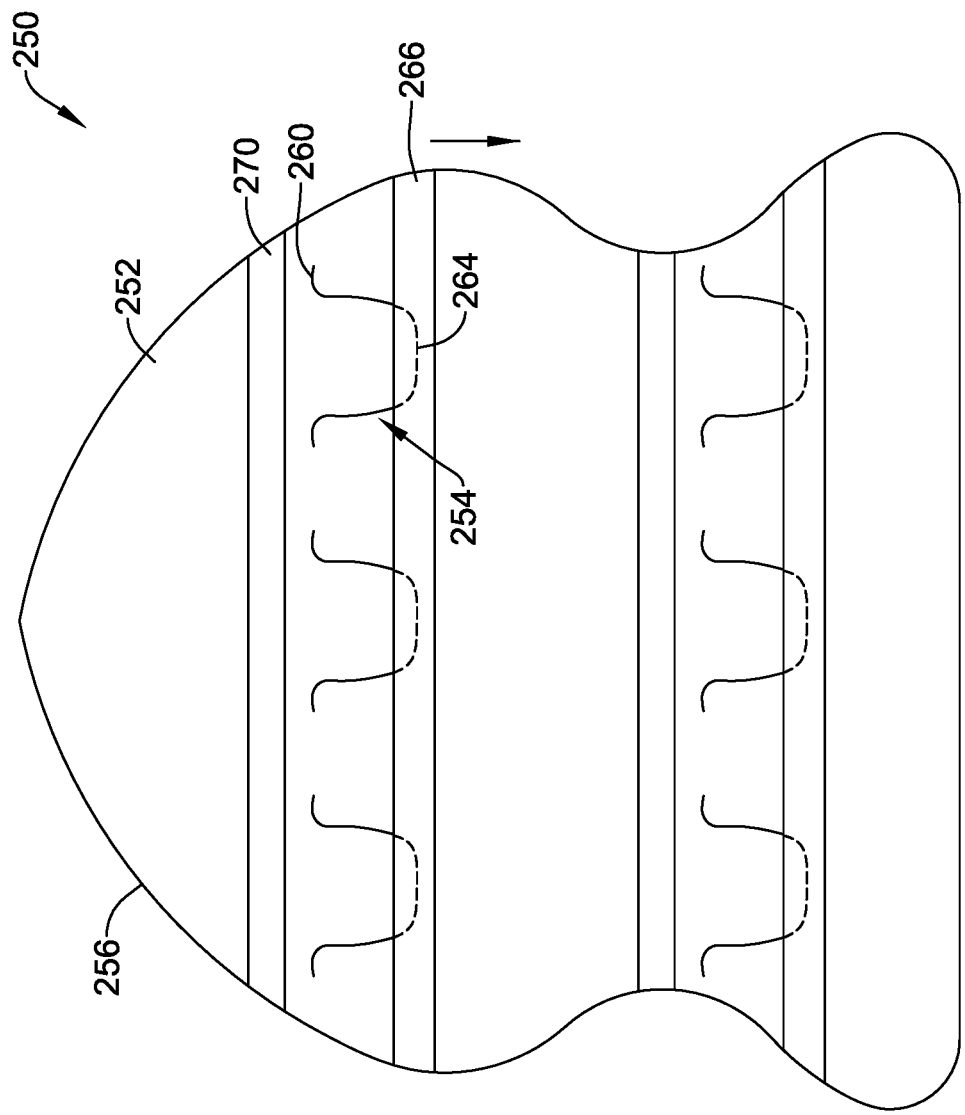
FIG. 7B illustrates a side view of the example occlusive implant of FIG. 7A in a deployed configuration.

FIG. 7A illustrates a side view of another example occlusive device 250 in a collapsed or delivery configuration. The occlusive device 250 may be similar in form and function to the occlusive device 10. For example, the occlusive device 250 may include an expandable member 252 and a plurality of fixation members or mechanisms 254 coupled thereto. While not explicitly shown, the expandable member 252 may include an inner cavity configured to receive an inflation fluid to expand the occlusive device from the collapsed delivery configuration to an expanded deployed configuration (as shown in FIG. 7B). The fixation members 254 made be formed from a metal (e.g., stainless steel), a composite, a shape memory material (e.g., Nitinol), a polymer (e.g., polyester, etc.) or combinations thereof.

Figure 7C:
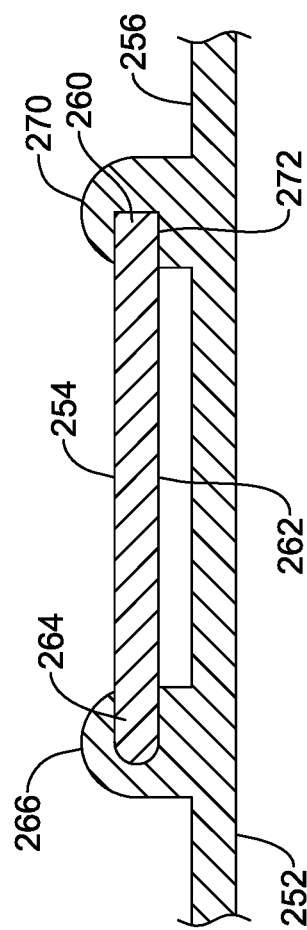
FIG. 7C illustrates a partial cross-section view of an illustrative fixation mechanism of FIG. 7A in a delivery configuration.

FIG. 7A illustrates six fixation members 254 however, it is contemplated that the occlusive device 250 may include any number of fixation members 254 distributed about the length and/or circumference, as desired. The plurality of fixation members 254 may be coupled to an outer surface 256 of the expandable member 252. In some embodiments, the fixation members 254 may have a generally u-shaped configuration extending from a first end 260 having two legs 262 and a curved second end region 264 connecting the legs 262. The second end region 264 may be embedded in a securement rib 266 formed in an outer surface of the expandable member 252. However, it is contemplated that the second end region 264 may be coupled to the expandable member 252 in any manner desired, including adhesives, heating bonding, and/or molding. FIG. 7C illustrates a partial cross-sectional view of the illustrative occlusive member 250 taken through a leg 262 of a fixation member 254 in a delivery configuration. As can be seen in FIG. 7C, the securement rib 266 may be a raised region extending from an outer surface 256 of the expandable member 252. The second end region 264 of the fixation mechanism 254 may be fixedly secured to the securement rib 266 such that movement of the securement rib 266 is translated to the fixation mechanism 254.

Figure 7D:
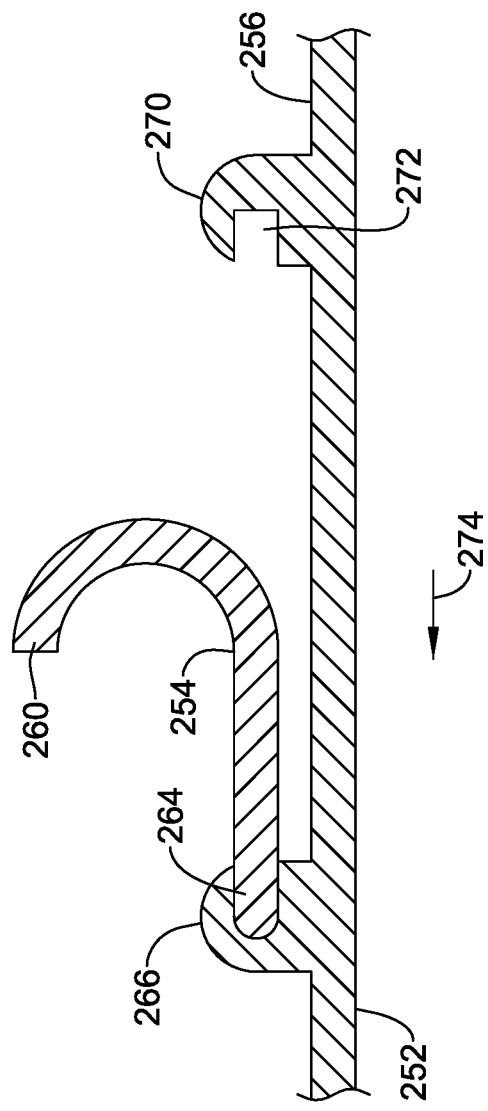
FIG. 7D illustrates a partial cross-section view of an illustrative fixation mechanism of FIG. 7B in a deployed configuration.

The occlusive device 250 may further include a sheathing rib 270 formed in an outer surface of the expandable member 252. As can be seen in FIG. 7C, the sheathing rib 270 may include a recess or cavity 272 formed therein and configured to receive the first end 260 of the fixation mechanism 254. It is contemplated that the first end 260 of the fixation member 254 may be pre-formed to extend radially away from the outer surface 256 of the expandable member 252. It is contemplated that sheathing rib 270 may exert a biasing force on the first end 260 of the fixation member 254 to maintain the first end 260 in a collapsed delivery configuration. As the occlusive device 250 is inflated or expanded, the shape of the expandable member 252 may begin to change, as shown in FIG. 7B, which illustrates a side view of the illustrative occlusive device 250 in an expanded or deployed configuration. As the pressure increases within the inflation cavity, the expandable member 252 begins to assume its expanded shape. In some instances, as the expandable member 252 is inflated, the outer surface 256 of the expandable member 252 assumes a curved profile. As the outer surface 256 changes shape, the first end 260 of the fixation member 254 is moved longitudinally away (e.g., by longitudinal distention) from the sheathing rib 270, as shown at arrow 274. FIG. 7D illustrates a partial cross-sectional view of the illustrative occlusive member 200 taken through a leg 262 of a fixation member 254 in an expanded or deployed configuration. Once the first end 260 of the fixation member 254 is no longer disposed within the cavity 272 of the sheathing rib 270, the first end 260 resumes its preformed state, as shown in FIGS. 7B and 7D. The pre-formed state may be such that the first end 260 is directed radially away from the expandable member 252 and towards a body tissue. As the expandable member 252 is inflated, the first end 260 of the fixation member 254 is moved towards and driven into adjacent tissue (once free from the sheathing rib 270) to help secure the occlusive device 250 within the LAA. It is contemplated that while the fixation member 254 and securement rib 266 (and/or sheathing rib 270) are described as mounted and movable longitudinally, the fixation member 254 and securement rib 266 (and/or sheathing rib 270) may be mounted such that radial distention deploys the first end 260 of the fixation member.

The securement rib 266 and sheathing rib 270 occlusive device 250 may extend around an entire circumference of the expandable member 252 or partially around a circumference, as desired. It is further contemplated that the securement rib 266 and sheathing rib 270 may be provided as pairs for each row of fixation members 254. While FIGS. 7A and 7B illustrate two rows of fixation members 254, the occlusive device 250 may include any number of rows of fixation members 254 desired, including fewer than two or more than two. Further, the fixation mechanisms 254 need not be provided as rows. A single fixation mechanism 254 may be provided at one or more longitudinal locations, if so desired.

In some examples, the fixation member 254 may be positioned between two layers of a multi-walled balloon. In such embodiments, the fixation member 254 may be configured to exit the outer layer upon expansion of the expandable member 252 through a preformed aperture or by puncturing a hole through the outermost layer. It is contemplated that the innermost layer may provide a fluid-tight seal such that inflation fluid remains within the inflation cavity.

Figure 8A:
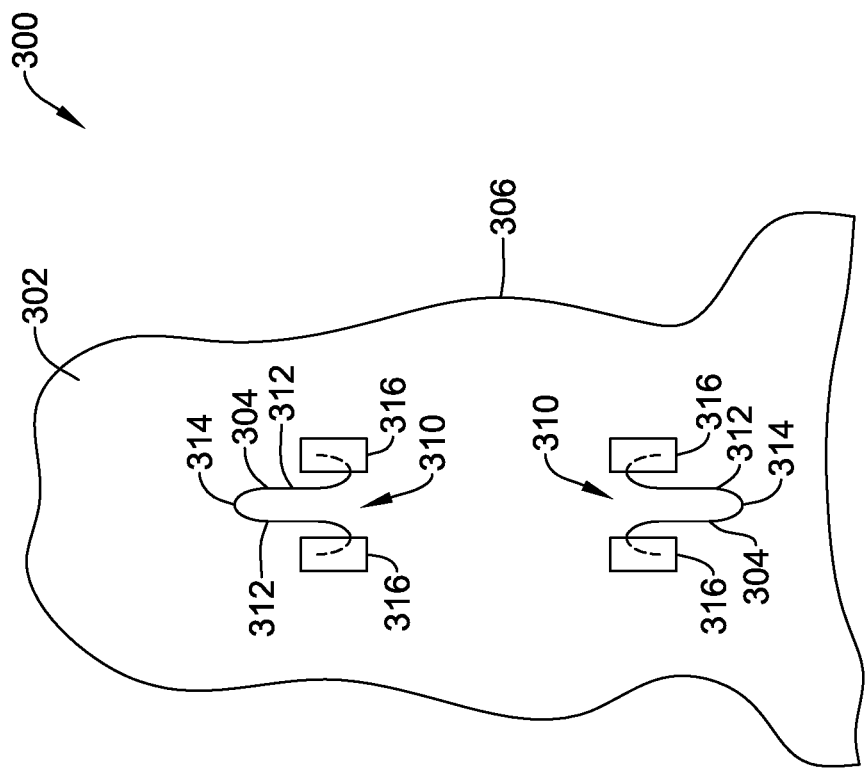
FIG. 8A illustrates a side view of another example occlusive implant in a delivery configuration.

FIG. 8A illustrates a side view of another example occlusive device 300 in a collapsed or delivery configuration. The occlusive device 300 may be similar in form and function to the occlusive device 10. For example, the occlusive device 300 may include an expandable member 302 and a plurality of fixation members or mechanisms 304 coupled thereto. While not explicitly shown, the expandable member 302 may include an inner cavity configured to receive an inflation fluid to expand the occlusive device from the collapsed delivery configuration to an expanded deployed configuration (as shown in FIG. 8B). The fixation members 304 made be formed from a metal (e.g., stainless steel), a composite, a shape memory material (e.g., Nitinol), a polymer (e.g., polyester, etc.) or combinations thereof.

FIG. 8A illustrates two fixation members 304 however, it is contemplated that the occlusive device 300 may include any number of fixation members 304 distributed about the length and/or circumference, as desired. The fixation members 304 may be coupled to an outer surface 306 of the expandable member 302. In some embodiments, the fixation members 304 may have a generally u-shaped configuration extending from a first end 310 having two legs 312 and a curved second end region 314 connecting the legs 312. The second end region 314 and/or a portion of the legs 312 adjacent to the second end region 314 may be embedded an outer surface 306 of the expandable member 302. However, it is contemplated that the second end region 314 and/or a portion of the legs 312 adjacent to the second end region 314 may be coupled to the expandable member 302 in any manner desired, including adhesives, heating bonding, molding, suturing, stitching, weaving, braiding, etc.

Figure 8C:
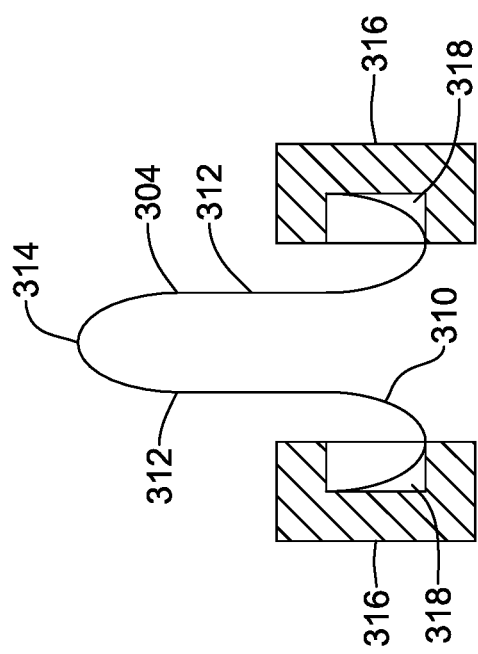
FIG. 8C illustrates a partial cross-section view of an illustrative fixation mechanism of FIG. 8A in a delivery configuration.

FIG. 8C illustrates a partial cross-sectional view of the illustrative occlusive member 300 taken through a pair of securement members 316 of the occlusive device 300 with the fixation member 304 in a delivery configuration. The securement members 316 may be a raised region extending from an outer surface 306 of the expandable member 302. The securement members 316 may each include a recess or cavity 318 formed therein and configured to receive the first end 310 of each leg 312 of the fixation mechanism 304. In some instances, the cavity 318 may extend through an entire width of the securement member 316 such that the first end 310 of the leg 312 of the fixation member 304 may be inserted from either side. In some cases, a securement member 316 may house more than fixation member 304 at a time. It is contemplated that the first end 310 of the fixation member 304 may be pre-formed to extend radially away from the outer surface 306 of the expandable member 302. The securement members 316 may exert a biasing force on the first end 310 of the fixation member 304 to maintain the first end 310 in a collapsed delivery configuration.

As the occlusive device 300 is inflated or expanded, the shape of the expandable member 302 may begin to change, as shown in FIG. 8B, which illustrates a side view of the illustrative occlusive device 300 in an expanded or deployed configuration. As the pressure increases within the inflation cavity, the expandable member 302 begins to assume its expanded shape. In some instances, as the expandable member 302 is inflated, the outer surface 306 of the expandable member 302 assumes a curved profile. As the outer surface 306 changes shape, securement members 316 are moved circumferentially away (e.g., by radial distention) from the first end 310 of the fixation member 304, as shown at arrow 320.

Figure 8D:
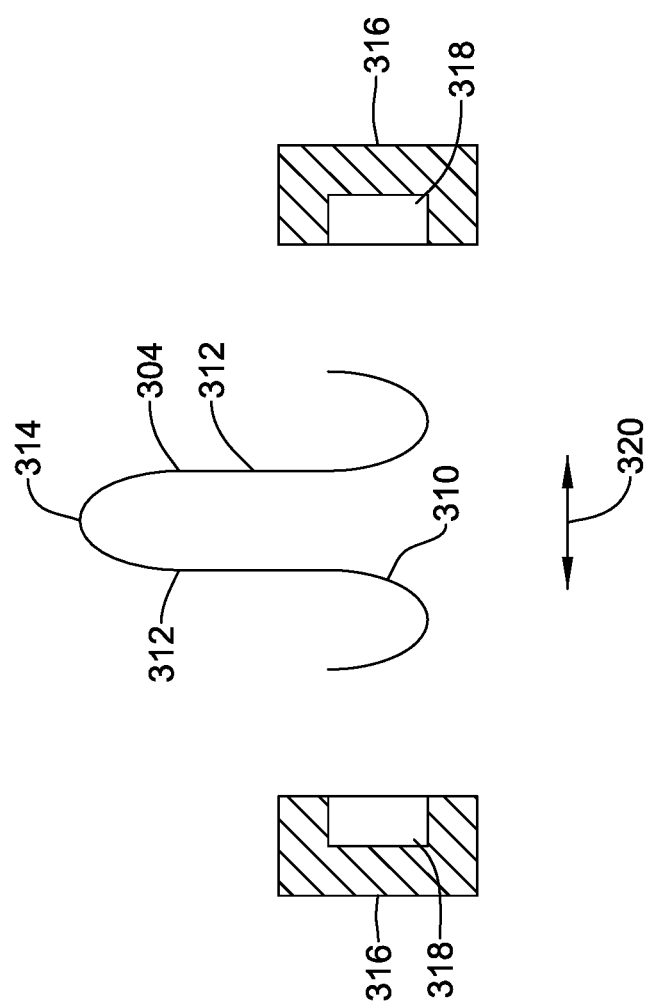
FIG. 8D illustrates a partial cross-section view of an illustrative fixation mechanism of FIG. 8B in a deployed configuration.

FIG. 8D illustrates a partial cross-sectional view of the illustrative occlusive member 300 taken through a pair of securement members 316 of the occlusive device 300 with the fixation member 304 in an expanded or deployed configuration. Once the first end 310 of the fixation member 304 is no longer disposed within the cavities 318 of the securement members 316, the first end 310 resumes its pre-formed state, as shown in FIGS. 8B and 8D. The pre-formed state may be such that the first end 310 is directed radially away from the expandable member 302 and towards a body tissue. As the expandable member 302 is inflated, the first end 310 of the fixation member 304 is moved towards and driven into adjacent tissue (once free from the securement members 316) to help secure the occlusive device 300 within the LAA. It is contemplated that while the fixation member 304 and securement members 316 are described as mounted and movable longitudinally, the fixation member 304 and securement members 316 may be mounted such that longitudinal distention deploys the first end 310 of the fixation member 304.

In some examples, the fixation member 304 may be positioned between two layers of a multi-walled balloon. In such embodiments, the fixation member 304 may be configured to exit the outer layer upon expansion of the expandable member 302 through a preformed aperture or by puncturing a hole through the outermost layer. It is contemplated that the innermost layer may provide a fluid-tight seal such that inflation fluid remains within the inflation cavity.

Figure 9A:
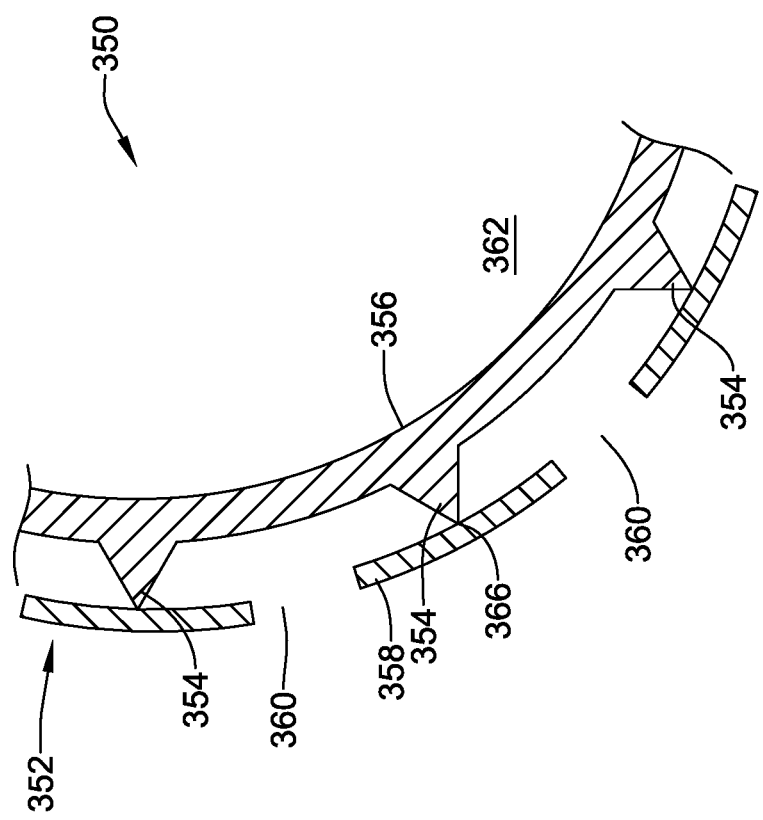
FIG. 9A illustrates a partial cross-sectional view of another example occlusive implant in a delivery configuration.
Figure 9B:
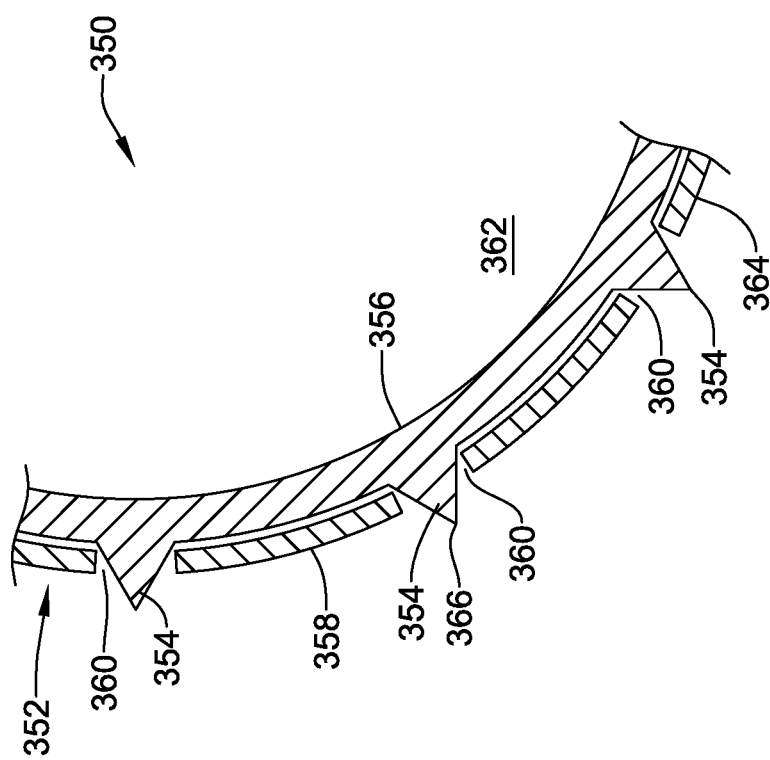
FIG. 9B illustrates a partial cross-sectional view of the example occlusive implant of FIG. 9A in a deployed configuration.

FIG. 9A illustrates a partial cross-sectional view of another example occlusive device 350 in a collapsed or delivery configuration. The occlusive device 350 may be similar in form and function to the occlusive device 10. For example, the occlusive device 350 may include an expandable member 352 and a plurality of fixation members or mechanisms 354 coupled thereto. The expandable member 352 may include an inner cavity 362 configured to receive an inflation fluid to expand the occlusive device from the collapsed delivery configuration to an expanded deployed configuration (as shown in FIG. 9B). The fixation members 354 made be formed from a metal (e.g., stainless steel), a composite, a shape memory material (e.g., Nitinol), a polymer (e.g., polyester, etc.) or combinations thereof.

The expandable member 352 may be formed from at least an inner layer 356 and an outer layer 358. The plurality of fixation members 354 may be coupled to or formed as a part of the inner layer 356, as desired. In some examples, the fixation members 354 may be formed as a separate structure from the inner layer 356 and subsequently coupled thereto using methods such as, but not limited to adhesives, melt bonding, overmolding, suturing, stitching, weaving, braiding, etc. In other examples, the fixation members 354 may be formed as a unitary structure with the inner layer 356. The outer layer 358 may include a plurality of apertures 360 extending from an inner surface to an outer surface thereof.

FIG. 9A illustrates a plurality of fixation members 354 however, it is contemplated that the occlusive device 350 may include any number of fixation members 354 distributed about the length and/or circumference, as desired. The fixation members 354 are illustrated as having a generally conical or pyramidal shape, however, it is contemplated that the fixation members 354 may take any shape desired. For example, the fixation members 354 may have a generally horseshoe or "U" shape similar to those described above. Other shapes are also contemplated including, but not limited to cylindrical, prism, etc.

As the occlusive device 350 is inflated or expanded, the shape of the expandable member 352 may begin to change, as shown in FIG. 9B, which illustrates a partial cross-sectional view of the illustrative occlusive device 350 in an expanded or deployed configuration. For example, as the pressure increases within the inflation cavity, the expandable member 352 begins to assume its expanded shape. In some embodiments, as the expandable member 352 is inflated, the inner layer 356 may shift or slide relative to the outer layer 358. As the inner layer 356 moves, the plurality of fixation mechanisms may slide into the apertures 360 such that they protrude radially beyond an outer surface 364 of the outer layer 358 of the expandable member 352. In some cases, hook barbs (as in a "u" shaped fixation mechanism) may be configured to extend through the apertures 360. It is contemplated that that the inner layer 356 and the outer layer 358 may be formed with different material properties. For example, the inner layer 356 and outer layer may have different elasticities such that the inner layer is more elastic. This may allow the fixation mechanisms 354 to shift towards the apertures 360 as the expandable member 352 is inflated.

As the expandable member 352 is inflated, the first end 366 of the fixation member 354 is moved towards and driven into adjacent tissue (once aligned with the apertures 360) to help secure the occlusive device 350 within the LAA. It is contemplated that while the fixation member 354 and securement members 316 are described as mounted and movable longitudinally, the fixation member 354 and securement members 316 may be mounted such that longitudinal distention deploys the first end 310 of the fixation member 354.

Figure 10:
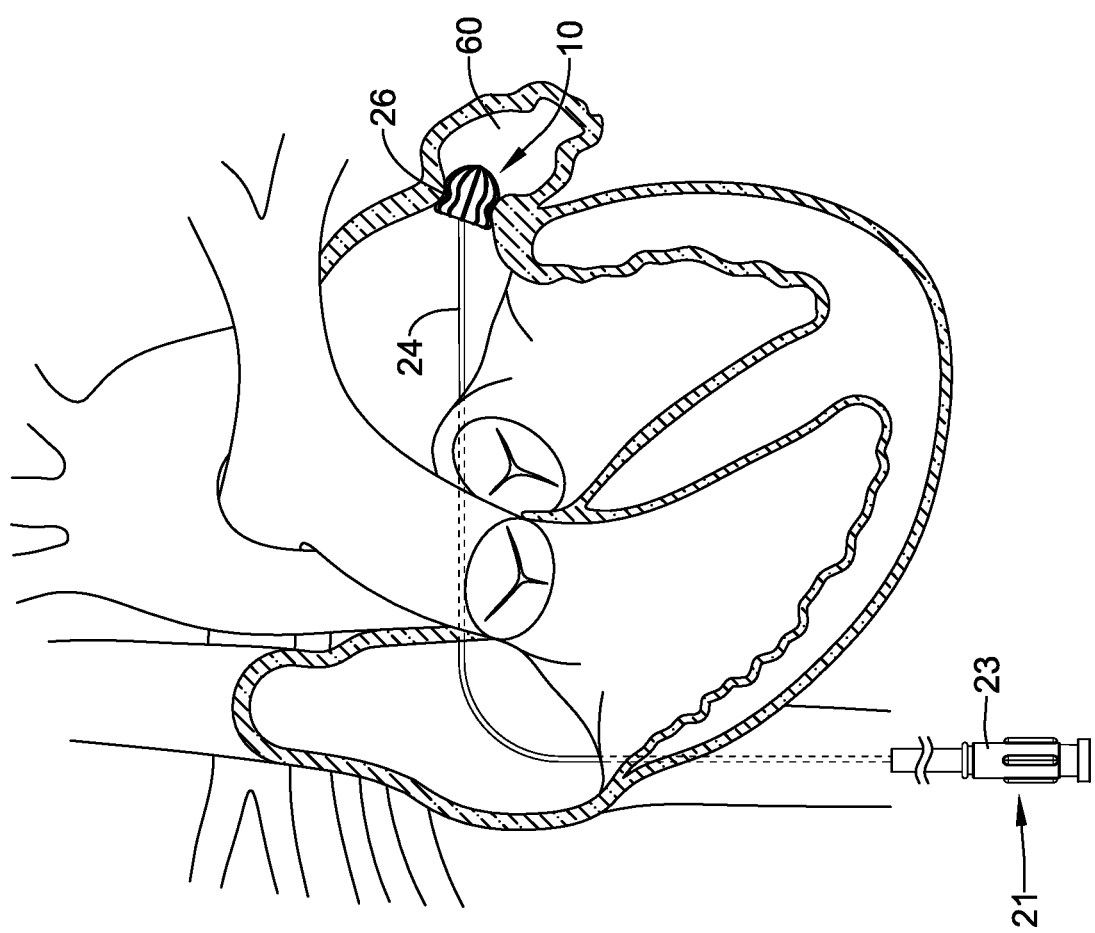
FIGS. 10-15 illustrate an example occlusive implant being positioned within an opening of the left atrial appendage.

FIG. 10 illustrates that the occlusive implant 10 may be inserted and advanced through a body lumen via an occlusive implant delivery system 21. FIG. 10 further illustrates the occlusive implant 10 positioned within the left atrial appendage 60. As discussed above, in some instances the occlusive implant 10 may be positioned within the left atrial appendage such that the nesting region 26 is anchored within a portion of the left atrial appendage 60. While the method and positioning is described with respect to occlusive implant 10, the method may be applicable to any of implants 10, 100, 150, 200, 250, 300, 350 described herein In some instances, an occlusive implant delivery system 21 may include a delivery catheter 24 which is guided toward the left atrium via various chambers and lumens of the heart (e.g., the inferior vena cava, the superior vena cava, the right atrium, etc.) to a position adjacent the left atrial appendage 60. The delivery system 21 may include a hub member 23 coupled to a proximal region of the delivery catheter 24. The hub member 23 may be manipulated by a clinician to direct the distal end region of the delivery catheter 24 to a position adjacent the left atrial appendage 60. As discussed above, a proximal end of the occlusive device 10 may be configured to releasably attach, join, couple, engage, or otherwise connect to the distal end of the delivery catheter 24. In some embodiments, an end region of the occlusive device 10 may include a threaded insert coupled thereto. In some embodiments, the threaded insert may be configured to and/or adapted to couple with, join to, mate with, or otherwise engage a threaded member disposed at the distal end of the delivery catheter 24. Other means of releasably coupling and/or engaging the proximal end of the occlusive device 10 to the distal end of the delivery catheter are also contemplated. Further, in some examples the delivery catheter 24 may include an inflation lumen (not show) designed to permit inflation media to pass into the occlusive device 10 (as described above). For example, in some examples, the distal end of the delivery catheter 24 may include a needle designed to be inserted through the valve 32 (discussed in FIG. 3).

Figure 11:
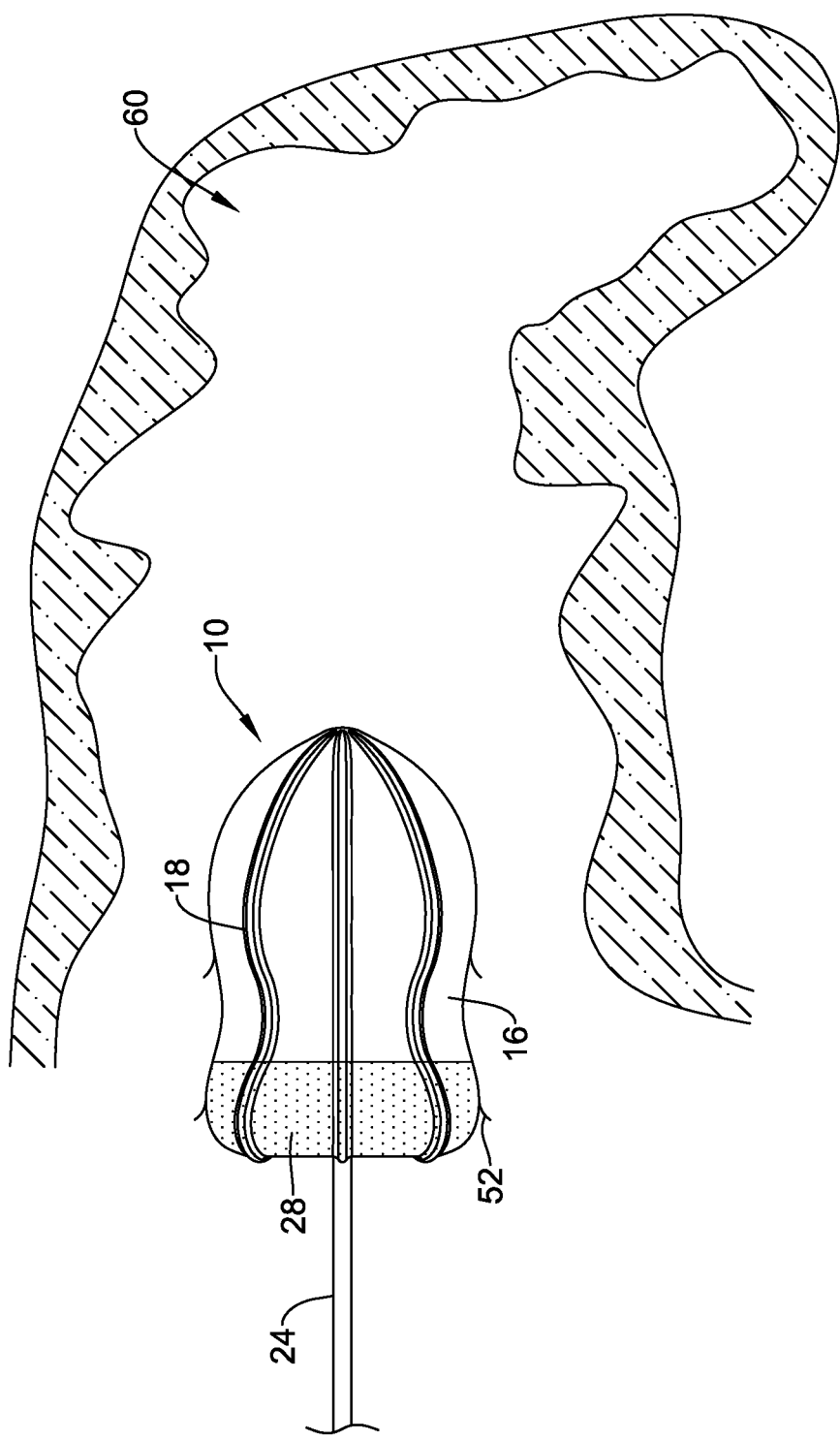
Figure 12:
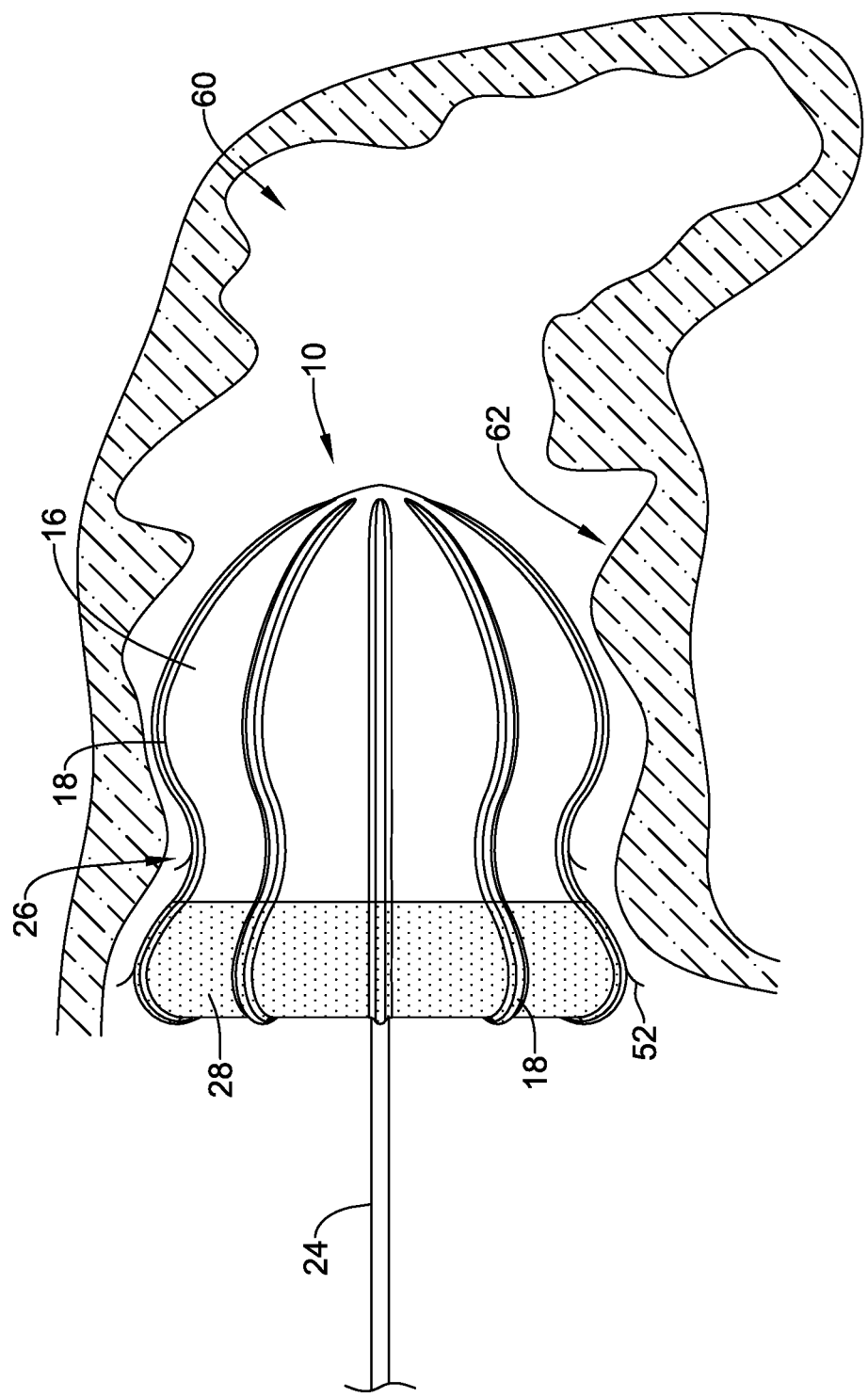
Figure 13:
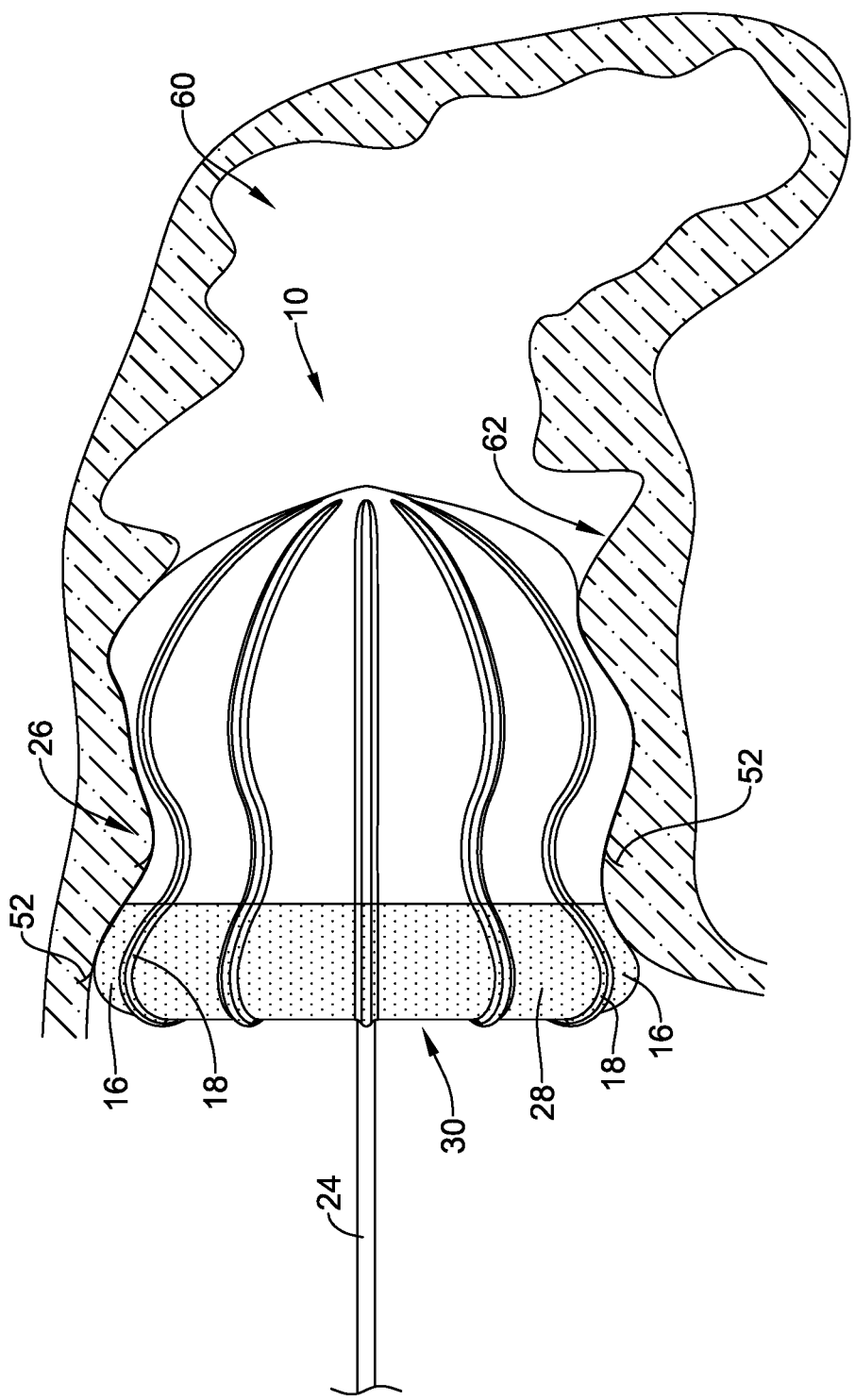

FIGS. 11-13 illustrate the example occlusive device 10 (described above) being positioned and deployed in an opening of the left atrial appendage 60. As discussed above, in some examples, the occlusive device 10 may be configured to shift between a collapsed configuration and an expanded configuration. For example, in some instances, the occlusive implant may be in a collapsed configuration during delivery via an occlusive device delivery system, whereby the occlusive device expands to an expanded configuration once deployed from the occlusion implant delivery system.

FIG. 11 shows the occlusive device 10 including an expandable member 16, a plurality of spine members 18 and a cellular-growth promoting coating 28 (as described above). Further, FIG. 11 illustrates that the occlusive member 10 may be detachably coupled to a delivery catheter 24. The occlusive member 10 shown in FIG. 11 may be described as being in a deflated or delivery configuration. In other words, the expandable member 16 may not contain any inflation media within its inner cavity. It can be appreciated that it may be desirable to maintain the occlusive member 10 in a collapsed configuration when delivering the occlusive member 10 to the target site (e.g., an opening in the left atrial appendage 60). A collapsed configuration may permit the occlusive member 10 to more easily track through tortuous vasculature as a clinician directs the device to the target site.

FIG. 12 illustrates an example first stage in deployment of the occlusive member 10. FIG. 12 shows the expandable member 16 expanded to a larger diameter as compared with the non-expanded configuration illustrated in FIG. 11. It can be appreciated that inflation media has been injected into the inner chamber of the expandable member 16, whereby the inflation media shifts the expandable member from the deflated configuration (shown in FIG. 11) to the partially-inflated configuration shown in FIG. 12.

Additionally, FIG. 12 illustrates that as the expandable member 16 inflates radially outward, the spine members 18 approach and may contact the inner surface 62 (e.g., the tissue wall) of the left atrial appendage 60. It can be appreciated that as the spine members 18 (which are circumferentially spaced around the expandable member 16) begin to contact the inner surface 62 of the left atrial appendage 60, they may center and maintain the occlusive device 10 within the opening of the left atrial appendage 60. Additionally, as the spine members 18 contact the inner surface 62 of the atrial appendage 60 they may reduce the likelihood that occlusive device 10 will shift its position within the left atrial appendage 60. Additionally, when aligned properly, the nesting region 26 of the occlusive member 10 may nest within a portion of the wall of the left atrial appendage 60, thereby furthering reducing the likelihood that the occlusive member 10 will shift its position while in the partially deflated state shown in FIG. 12.

FIG. 13 illustrates the occlusive member 10 in a fully inflated state. Additionally, FIG. 13 illustrates that the expandable member 16 may be compliant and, therefore, substantially conform to and/or be in sealing engagement with the shape and/or geometry of a lateral wall 62 of a left atrial appendage 60 while in the inflated (e.g., expanded) configuration. In some embodiments, the occlusive device 10 may expand to a size, extent, or shape different from a maximum unconstrained extent, as determined by the surrounding tissue and/or lateral wall 62 of the left atrial appendage 60.

As can be appreciated from FIG. 13, continued inflation of the expandable member 16 beyond the partially inflated state shown in FIG. 12 may permit the expandable member 16 to expand and conform to the specific geometry of the inner surface 62 of the left atrial appendage 60. In other words, as inflation media is added to the expandable member 16, the expandable member 16 may fill and/or seal gaps in the opening of the left atrial appendage 60 which may not have been sealed while the occlusive device 10 was partially inflated (as shown in FIG. 12). It can be appreciated that the flexible material used to construct the expandable member 16 may stretch, conform and directly oppose the folded curvature of the inner surface 62 of the left atrial appendage 60. For example, FIG. 13 shows the expandable member 16 expanded such that the expandable member 16 is contacting the curved inner surface 62 of the left atrial appendage 60, thereby sealing the opening of the left atrial appendage 60. Additionally, FIG. 13 illustrates the nesting region 26 of the occlusive member seated within a portion of the inner surface 62 of the left atrial appendage 60.

It can further be appreciated from FIG. 13 that the bottom surface 30 of the occlusive device is positioned such that it is facing the left atrium of the heart. As discussed above, the bottom surface 30 of the occlusive device 10 may include the cellular-growth promoting coating 28. Accordingly, the cellular-growth promoting coating 28 is positioned to promote the growth of endothelial cellular tissue across the bottom surface 30 of the occlusive implant 10, thereby effectively sealing the left atrial appendage 60.

Figure 14:
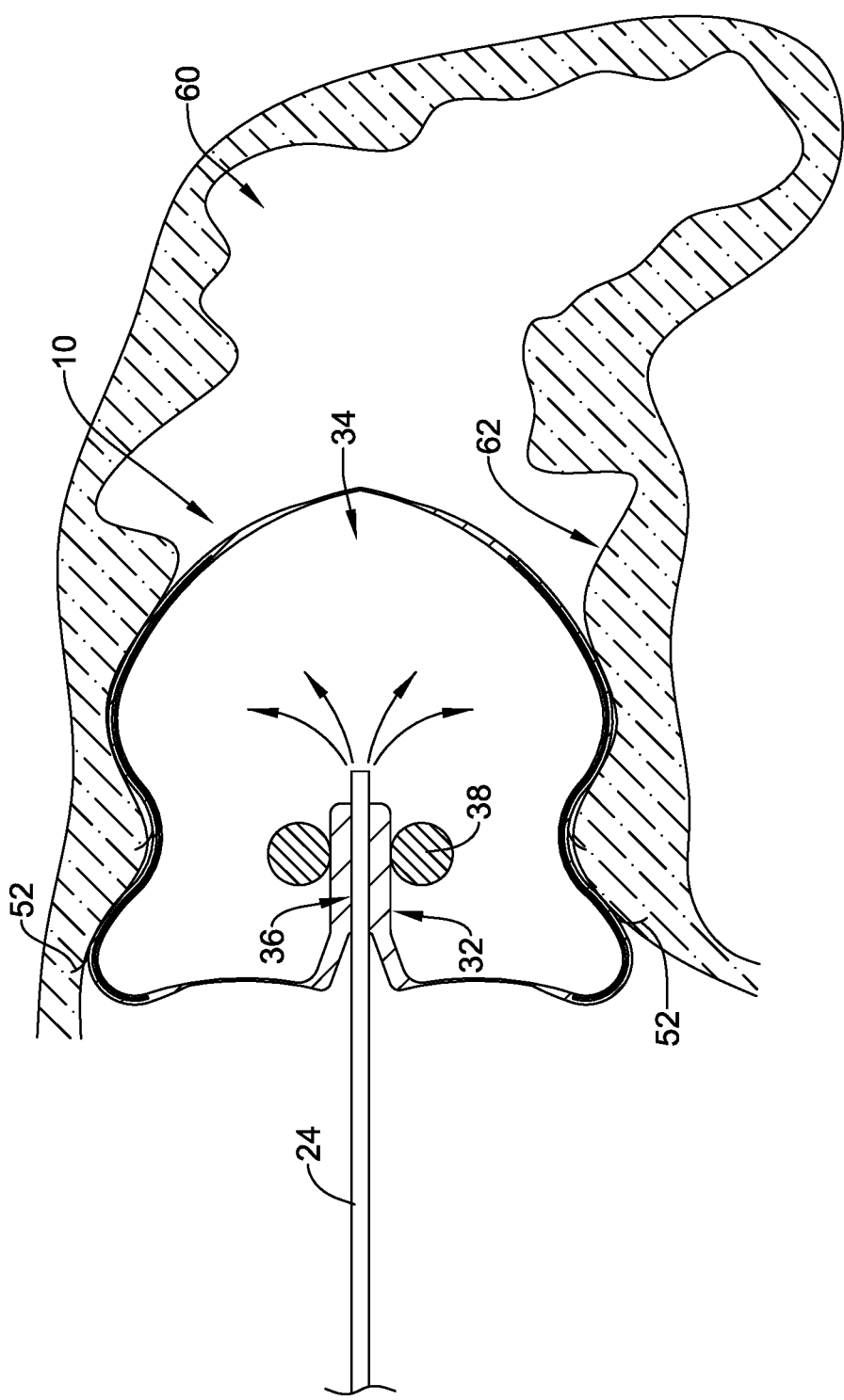
Figure 15:
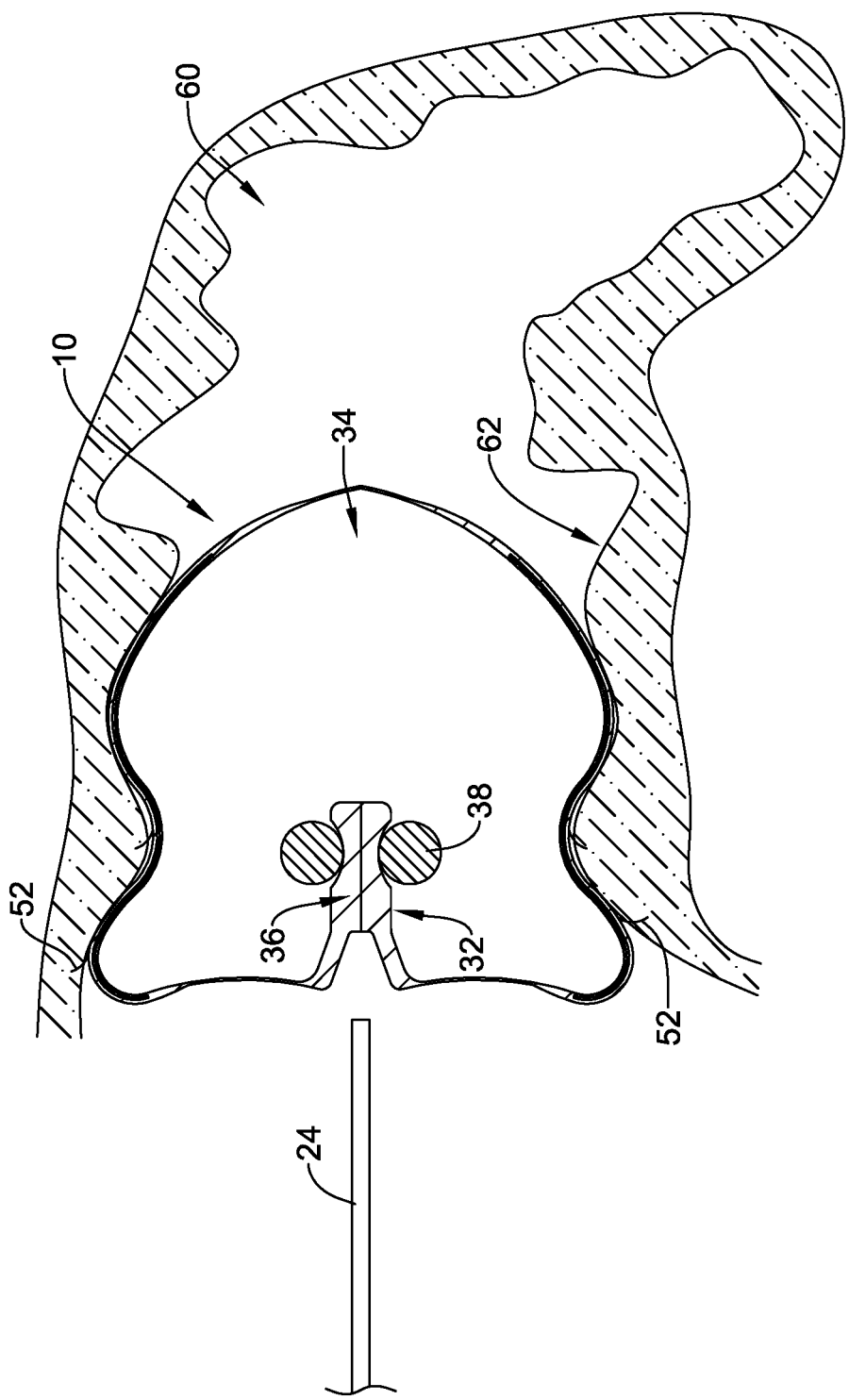

FIG. 14 and FIG. 15 show cross-sectional views of the occlusive device 10 being inflated from a partially-inflated state (shown in FIG. 12) to a fully inflated state (shown in FIG. 13) whereby the expandable member 16 fully opposes the inner surface 62 of the left atrial appendage 60. FIG. 14 further illustrates a delivery catheter 24 (described above in some examples as a secondary medical device) having been advanced through the lumen 36 of the valve 32. As described above, the O-ring 38 has expanded radially outward to permit the distal end region of the delivery catheter 24 to be advanced through the valve lumen 36 and into the inner chamber 34 of the expandable member 16. Once positioned within the inner chamber 34, the inflation media (depicted by the arrows in FIG. 14) may be injected into the inner chamber 34, thereby expanding the occlusive device 10 as described above. As the occlusive device 10 is inflated, the fixation members 52 may be deployed into the tissue 62 using any of the methods and structures described herein.

FIG. 15 shows the occlusive device 10 deployed along the inner surface 62 of the left atrial appendage 60. Further, FIG.

15 illustrates the delivery catheter 24 described above in FIG. 14 having been removed from the inflation lumen 36 of the valve 32. It can be appreciated from FIG. 15 that the O-ring 38 has been compressed radially inward such that it has closed the lumen 36. It can be further appreciated that the O-ring 38 may designed to exert sufficient radially inward force along the valve 36 to prevent the inflation media from passing back through the valve 32 (which may partially collapse the occlusive device 10).

The materials that can be used for the various components of the occlusive implant 10 (and variations, systems or components thereof disclosed herein) and the various elements thereof disclosed herein may include those commonly associated with medical devices. For simplicity purposes, the following discussion makes reference to the occlusive implant 10 (and variations, systems or components disclosed herein). However, this is not intended to limit the devices and methods described herein, as the discussion may be applied to other elements, members, components, or devices disclosed herein.

In some embodiments, the occlusive implant 10 (and variations, systems or components thereof disclosed herein) may be made from a metal, metal alloy, polymer (some examples of which are disclosed below), a metal-polymer composite, ceramics, combinations thereof, and the like, or other suitable material. Some examples of suitable metals and metal alloys include stainless steel, such as 444V, 444L, and 314LV stainless steel; mild steel; nickel-titanium alloy such as linear-elastic and/or super-elastic nitinol; other nickel alloys such as nickel-chromium-molybdenum alloys (e.g., UNS: N06625 such as INCONEL® 625, UNS: N06022 such as HASTELLOY® C-22®, UNS: N10276 such as HASTELLOY® C276®, other HASTELLOY® alloys, and the like), nickel-copper alloys (e.g., UNS: N04400 such as MONEL® 400, NICKELVAC® 400, NICORROS® 400, and the like), nickel-cobalt-chromium-molybdenum alloys (e.g., UNS: R44035 such as MP35-N® and the like), nickel-molybdenum alloys (e.g., UNS: N10665 such as HASTELLOY® ALLOY B2®), other nickel-chromium alloys, other nickel-molybdenum alloys, other nickel-cobalt alloys, other nickel-iron alloys, other nickel-copper alloys, other nickel-tungsten or tungsten alloys, and the like; cobalt-chromium alloys; cobalt-chromium-molybdenum alloys (e.g., UNS: R44003 such as ELGILOY®, PHYNOX®, and the like); platinum enriched stainless steel; titanium; platinum; palladium; gold; combinations thereof; and the like; or any other suitable material.

As alluded to herein, within the family of commercially available nickel-titanium or nitinol alloys, is a category designated "linear elastic" or "non-super-elastic" which, although may be similar in chemistry to conventional shape memory and super elastic varieties, may exhibit distinct and useful mechanical properties. Linear elastic and/or non-super-elastic nitinol may be distinguished from super elastic nitinol in that the linear elastic and/or non-super-elastic nitinol does not display a substantial "superelastic plateau" or "flag region" in its stress/strain curve like super elastic nitinol does. Instead, in the linear elastic and/or non-super-elastic nitinol, as recoverable strain increases, the stress continues to increase in a substantially linear, or a somewhat, but not necessarily entirely linear relationship until plastic deformation begins or at least in a relationship that is more linear than the super elastic plateau and/or flag region that may be seen with super elastic nitinol. Thus, for the purposes of this disclosure linear elastic and/or non-super-elastic nitinol may also be termed "substantially" linear elastic and/or non-super-elastic nitinol.

In some cases, linear elastic and/or non-super-elastic nitinol may also be distinguishable from super elastic nitinol in that linear elastic and/or non-super-elastic nitinol may accept up to about 2-5% strain while remaining substantially elastic (e.g., before plastically deforming) whereas super elastic nitinol may accept up to about 8% strain before plastically deforming. Both of these materials can be distinguished from other linear elastic materials such as stainless steel (that can also be distinguished based on its composition), which may accept only about 0.2 to 0.44 percent strain before plastically deforming.

In some embodiments, the linear elastic and/or non-super-elastic nickel-titanium alloy is an alloy that does not show any martensite/austenite phase changes that are detectable by differential scanning calorimetry (DSC) and dynamic metal thermal analysis (DMTA) analysis over a large temperature range. For example, in some embodiments, there may be no martensite/austenite phase changes detectable by DSC and DMTA analysis in the range of about −60 degrees Celsius (° C.) to about 120° C. in the linear elastic and/or non-super-elastic nickel-titanium alloy. The mechanical bending properties of such material may therefore be generally inert to the effect of temperature over this very broad range of temperature. In some embodiments, the mechanical bending properties of the linear elastic and/or non-super-elastic nickel-titanium alloy at ambient or room temperature are substantially the same as the mechanical properties at body temperature, for example, in that they do not display a super-elastic plateau and/or flag region. In other words, across a broad temperature range, the linear elastic and/or non-super-elastic nickel-titanium alloy maintains its linear elastic and/or non-super-elastic characteristics and/or properties.

In some embodiments, the linear elastic and/or non-super-elastic nickel-titanium alloy may be in the range of about 50 to about 60 weight percent nickel, with the remainder being essentially titanium. In some embodiments, the composition is in the range of about 54 to about 57 weight percent nickel. One example of a suitable nickel-titanium alloy is FHP-NT alloy commercially available from Furukawa Techno Material Co. of Kanagawa, Japan. Other suitable materials may include ULTANIUM™ (available from Neo-Metrics) and GUM METAL™ (available from Toyota). In some other embodiments, a superelastic alloy, for example a superelastic nitinol can be used to achieve desired properties.

In at least some embodiments, portions or all of the occlusive implant 10 (and variations, systems or components thereof disclosed herein) may also be doped with, made of, or otherwise include a radiopaque material. Radiopaque materials are understood to be materials capable of producing a relatively bright image on a fluoroscopy screen or another imaging technique during a medical procedure. This relatively bright image aids a user in determining the location of the occlusive implant 10 (and variations, systems or components thereof disclosed herein). Some examples of radiopaque materials can include, but are not limited to, gold, platinum, palladium, tantalum, tungsten alloy, polymer material loaded with a radiopaque filler, and the like. Additionally, other radiopaque marker bands and/or coils may also be incorporated into the design of the occlusive implant 10 (and variations, systems or components thereof disclosed herein). to achieve the same result.

In some embodiments, a degree of Magnetic Resonance Imaging (MM) compatibility is imparted into the occlusive implant 10 (and variations, systems or components thereof disclosed herein). For example, the occlusive implant 10 (and variations, systems or components thereof disclosed herein) and/or components or portions thereof, may be made of a material that does not substantially distort the image and create substantial artifacts (e.g., gaps in the image). Certain ferromagnetic materials, for example, may not be suitable because they may create artifacts in an MRI image. The occlusive implant 10 (and variations, systems or components disclosed herein) or portions thereof, may also be made from a material that the MRI machine can image. Some materials that exhibit these characteristics include, for example, tungsten, cobalt-chromium-molybdenum alloys (e.g., UNS: R44003 such as ELGILOY®, PHYNOX®, and the like), nickel-cobalt-chromium-molybdenum alloys (e.g., UNS: R44035 such as MP35-N® and the like), nitinol, and the like, and others.

In some embodiments, the occlusive implant 10 (and variations, systems or components thereof disclosed herein) and/or portions thereof, may be made from or include a polymer or other suitable material. Some examples of suitable polymers may include copolymers, polyisobutylene-polyurethane, polytetrafluoroethylene (PTFE), ethylene tetrafluoroethylene (ETFE), fluorinated ethylene propylene (FEP), polyoxymethylene (POM, for example, DELRIN® available from DuPont), polyether block ester, polyurethane (for example, Polyurethane 85A), polypropylene (PP), polyvinylchloride (PVC), polyether-ester (for example, ARNITEL® available from DSM Engineering Plastics), ether or ester based copolymers (for example, butylene/poly(alkylene ether) phthalate and/or other polyester elastomers such as HYTREL® available from DuPont), polyamide (for example, DURETHAN® available from Bayer or CRISTAMID® available from Elf Atochem), elastomeric polyamides, block polyamide/ethers, polyether block amide (PEBA, for example available under the trade name PEBAX®), ethylene vinyl acetate copolymers (EVA), silicones, polyethylene (PE), Marlex high-density polyethylene, Marlex low-density polyethylene, linear low density polyethylene (for example REXELL®), polyester, polybutylene terephthalate (PBT), polyethylene terephthalate (PET), polytrimethylene terephthalate, polyethylene naphthalate (PEN), polyetheretherketone (PEEK), polyimide (PI), polyetherimide (PEI), polyphenylene sulfide (PPS), polyphenylene oxide (PPO), poly paraphenylene terephthalamide (for example, KEVLAR®), polysulfone, nylon, nylon-12 (such as GRILAMID® available from EMS American Grilon), perfluoro(propyl vinyl ether) (PFA), ethylene vinyl alcohol, polyolefin, polystyrene, epoxy, polyvinylidene chloride (PVdC), poly(styrene-b-isobutylene-b-styrene) (for example, SIBS and/or SIBS 50A), polycarbonates, ionomers, polyurethane silicone copolymers (for example, ElastEon® from Aortech Biomaterials or ChronoSil® from AdvanSource Biomaterials), biocompatible polymers, other suitable materials, or mixtures, combinations, copolymers thereof, polymer/metal composites, and the like. In some embodiments, the sheath can be blended with a liquid crystal polymer (LCP). For example, the mixture can contain up to about 6 percent LCP.

In some embodiments, the occlusive implant 10 (and variations, systems or components thereof disclosed herein) may include a textile material. Some examples of suitable textile materials may include synthetic yarns that may be flat, shaped, twisted, textured, pre-shrunk or un-shrunk. Synthetic biocompatible yarns suitable for use in the present disclosure include, but are not limited to, polyesters, including polyethylene terephthalate (PET) polyesters, polypropylenes, polyethylenes, polyurethanes, polyolefins, polyvinyls, polymethylacetates, polyamides, naphthalene dicarboxylene derivatives, natural silk, and polytetrafluoroethylenes. Moreover, at least one of the synthetic yarns may be a metallic yarn or a glass or ceramic yarn or fiber. Useful metallic yarns include those yarns made from or containing stainless steel, platinum, gold, titanium, tantalum or a Ni—Co—Cr-based alloy. The yarns may further include carbon, glass or ceramic fibers. Desirably, the yarns are made from thermoplastic materials including, but not limited to, polyesters, polypropylenes, polyethylenes, polyurethanes, polynaphthalenes, polytetrafluoroethylenes, and the like. The yarns may be of the multifilament, monofilament, or spun-types. The type and denier of the yarn chosen may be selected in a manner which forms a biocompatible and implantable prosthesis and, more particularly, a vascular structure having desirable properties.

In some embodiments, the occlusive implant 10 (and variations, systems or components thereof disclosed herein) may include and/or be treated with a suitable therapeutic agent. Some examples of suitable therapeutic agents may include anti-thrombogenic agents (such as heparin, heparin derivatives, urokinase, and PPack (dextrophenylalanine proline arginine chloromethylketone)); anti-proliferative agents (such as enoxaparin, angiopeptin, monoclonal antibodies capable of blocking smooth muscle cell proliferation, hirudin, and acetylsalicylic acid); anti-inflammatory agents (such as dexamethasone, prednisolone, corticosterone, budesonide, estrogen, sulfasalazine, and mesalamine); anti-neoplastic/antiproliferative/anti-mitotic agents (such as paclitaxel, 5-fluorouracil, cisplatin, vinblastine, vincristine, epothilones, endostatin, angiostatin and thymidine kinase inhibitors); anesthetic agents (such as lidocaine, bupivacaine, and ropivacaine); anti-coagulants (such as D-Phe-Pro-Arg chloromethyl keton, an RGD peptide-containing compound, heparin, anti-thrombin compounds, platelet receptor antagonists, anti-thrombin antibodies, anti-platelet receptor antibodies, aspirin, prostaglandin inhibitors, platelet inhibitors, and tick antiplatelet peptides); vascular cell growth promoters (such as growth factor inhibitors, growth factor receptor antagonists, transcriptional activators, and translational promoters); vascular cell growth inhibitors (such as growth factor inhibitors, growth factor receptor antagonists, transcriptional repressors, translational repressors, replication inhibitors, inhibitory antibodies, antibodies directed against growth factors, bifunctional molecules consisting of a growth factor and a cytotoxin, bifunctional molecules consisting of an antibody and a cytotoxin); cholesterol-lowering agents; vasodilating agents; and agents which interfere with endogenous vasoactive mechanisms.

While the discussion above is generally directed toward an occlusive implant for use in the left atrial appendage of the heart, the aforementioned features may also be useful in other types of medical implants where a fabric or membrane is attached to a frame or support structure including, but not limited to, implants for the treatment of aneurysms (e.g., abdominal aortic aneurysms, thoracic aortic aneurysms, etc.), replacement valve implants (e.g., replacement heart valve implants, replacement aortic valve implants, replacement mitral valve implants, replacement vascular valve implants, etc.), and/or other types of occlusive devices (e.g., atrial septal occluders, cerebral aneurysm occluders, peripheral artery occluders, etc.). Other useful applications of the disclosed features are also contemplated.

It should be understood that this disclosure is, in many respects, only illustrative. Changes may be made in details, particularly in matters of shape, size, and arrangement of steps without exceeding the scope of the disclosure. This may include, to the extent that it is appropriate, the use of any of the features of one example embodiment being used in other embodiments. The disclosure's scope is, of course, defined in the language in which the appended claims are expressed.

What is claimed:

1. A medical device adapted to occlude a left atrial appendage, comprising:
    an expandable member having an outer surface, a first end region, a second end region;
    at least one fixation member having a first end and a second end coupled to the expandable member, the at least one fixation member configured to move from a delivery configuration to a deployed configuration in response to an expansion of the expandable member;
    a first retention sheath fixed to the outer surface of the expandable member,
    wherein when the at least one fixation member is in the delivery configuration the first end of the at least one fixation member is disposed within the first retention sheath and is biased into the delivery configuration; and
    wherein the expandable member is configured to expand and seal an opening of the left atrial appendage;
    wherein the first end of the at least one fixation member is configured to engage a tissue when the at least one fixation member is in the deployed configuration.

2. The medical device of claim 1, wherein when the at least one fixation member is in the delivery configuration the first end of the at least one fixation member extends approximately parallel to a longitudinal axis of the expandable member and when the at least one fixation member is in the deployed configuration the first end of the at least one fixation member extends at a non-parallel angle to the longitudinal axis and radially away from an outer surface of the expandable member.

3. The medical device of claim 1, wherein the first end of the at least one fixation member is pre-formed to extend radially away from the outer surface of the expandable member.

4. The medical device of claim 1, further comprising a first retention sheath defining a lumen and coupled to an outer surface of the expandable member and a second retention sheath defining a lumen and coupled to the outer surface of the expandable member, the first and second retention sheath being longitudinally aligned.

5. The medical device of claim 4, wherein the at least one fixation member comprises a first fixation member and a second fixation member.

6. The medical device of claim 5, wherein when the first and second fixation members are in the delivery configuration a first end of the first fixation member is disposed within the lumen of the second retention sheath, an intermediate portion of the first fixation member is disposed within the lumen of the first retention sheath, a first end of the second fixation member is disposed within the lumen of the first retention sheath, and an intermediate portion of the second fixation member is disposed within the lumen of the second retention sheath.

7. A medical device adapted to occlude a left atrial appendage, comprising:
    an expandable member having a first end region, a second end region;
    at least one fixation member having a first leg, a second leg, and a curved connection region connecting a second end of the first leg and a second end of the second leg, the at least one fixation member configured to move from a delivery configuration to a deployed configuration in response to an expansion of the expandable member;
    wherein the curved connection region is embedded in a securement rib, the securement rib extending circumferentially about the expandable member; and
    wherein the expandable member is configured to expand and seal an opening of the left atrial appendage.

8. The medical device of claim 7, wherein a first end of the first leg and a first end of the second leg are each pre-formed to extend radially away from an outer surface of the expandable member.

9. The medical device of claim 8, wherein the curved connection region is coupled to the outer surface of the expandable member.

10. The medical device of claim 9, wherein when in the delivery configuration the first ends of the first and second legs are disposed within a cavity in a first securement member and a cavity in a second securement member, respectively, the second securement member circumferentially spaced from the first securement member.

11. The medical device of claim 7, wherein when in the delivery configuration the first ends of the first and second legs are disposed within a cavity in a sheathing rib extending circumferentially about the expandable member and longitudinally spaced from the securement rib.

12. A medical device adapted to occlude a left atrial appendage, comprising:
    an expandable member including an inner layer and an outer layer and having a first end region, a second end region, wherein the outer layer includes at least one aperture extending from an inner surface to an outer surface of the outer layer;
    at least one fixation member having a first end and a second end coupled to the expandable member, the at least one fixation member configured to move from a delivery configuration to a deployed configuration in response to an expansion of the expandable member, wherein the at least one fixation member is configured to extend through the at least one aperture in the outer layer when the at least one fixation member is in the deployed configuration; and
    wherein the expandable member is configured to expand and seal an opening of the left atrial appendage.

13. The medical device of claim 12, wherein the at least one fixation member extends radially from the inner layer towards the outer layer.

* * * * *